(12) United States Patent
Anazawa et al.

(10) Patent No.: US 6,274,359 B1
(45) Date of Patent: Aug. 14, 2001

(54) 25-HYDROXYVITAMIN $D_3$-1α-HYDROXYLASE AND DNA ENCODING THE HYDROXYLASE

(75) Inventors: Hideharu Anazawa; Hiroko Shimada, both of Tokyo; Seiji Sugimoto, Hachioji; Tatsuo Suda, Tachikawa; Toshimasa Shinki, Tokyo; Takao Saruta, Tokyo; Yuzuru Ishimura, Mitaka; Matsuhiko Hayashi, Tokyo; Shu Wakino, Tokyo; Toshiaki Monkawa, Tokyo; Tadashi Yoshida, Tokyo; Hiromichi Suzuki, Tokyo, all of (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/111,730

(22) Filed: Jul. 8, 1998

(30) Foreign Application Priority Data

Jul. 10, 1997 (JP) .................................................. 9-185399
Nov. 25, 1997 (JP) .................................................. 9-322651

(51) Int. Cl.⁷ ............................. C12N 9/02; C12N 12/53; C12N 15/70; C12N 15/79; C12P 33/12
(52) U.S. Cl. ........................ 435/189; 435/69.1; 435/156; 435/252.3; 435/252.33; 435/320.1; 536/23.2
(58) Field of Search ................................. 435/189, 69.1, 435/252.3, 252.33, 320.1, 69.4; 536/23.2

(56) References Cited

U.S. PATENT DOCUMENTS

| | | | |
|---|---|---|---|
| 4,554,106 | 11/1985 | Deluca et al. ..................... 260/397.2 |
| 5,593,833 | * 1/1997 | Morrison et al. ........................ 435/6 |
| 5,786,191 | * 7/1998 | Goldstein et al. .................... 435/189 |
| 5,981,176 | * 11/1999 | Wallace .................................. 435/6 |
| 6,096,876 | * 8/2000 | St-Arnaud et al. ................. 536/23.2 |

FOREIGN PATENT DOCUMENTS

| | | |
|---|---|---|
| 0 477 961 | 4/1992 | (EP) . |
| 1 024 193 | 8/2000 | (EP) . |
| WO 99/05292 | 2/1999 | (WO) . |
| WO 99/07835 | 2/1999 | (WO) . |
| WO 99/49027 | 9/1999 | (WO) . |

OTHER PUBLICATIONS

Proc. Natl. Acad. Sci. USA, vol. 94, pp. 12920–12925 (Nov. 1997).
Journal of Bone and Mineral Research, vol. 11, pp. s124, 1996 (Abstract).
Database WPI, Week 9148, AN 91–349005 (1991) (Abstract Only).

(List continued on next page.)

Primary Examiner—Ponnathapu Achutamurthy
Assistant Examiner—William W. Moore
(74) Attorney, Agent, or Firm—Fitzpatrick, Cella, Harper & Scinto

(57) ABSTRACT

The present invention relates to a polypeptide having 25-hydroxyvitamin $D_3$-1α-hydroxylase activity, being useful for the prevention, diagnosis and therapeutic treatment of adult diseases such as osteoporosis induced by the decrease of active type vitamin $D_3$ and catalyzing the final stage of vitamin $D_3$ activation; and the gene encoding the polypeptide.

In accordance with the present invention, the following can be provided; a polypeptide having 25-hydroxyvitamin $D_3$-1α-hydroxylase activity, DNA encoding the polypeptide, a recombinant DNA prepared by inserting the DNA in a vector, a transformant carrying the recombinant DNA, a method for preparing 25-hydroxyvitamin $D_3$-1α-hydroxylase by using the transformant, a method for preparing 1α, 25-dihydroxyvitamin $D_3$ comprising using the polypeptide having 25-hydroxyvitamin $D_3$-1α-hydroxylase activity, and an antibody recognizing the polypeptide.

9 Claims, 1 Drawing Sheet

OTHER PUBLICATIONS

Journal of Endocrinology, vol. 154, pp. s75–s78, 1997.
DNA and Cell Biology, vol. 16, No. 12, pp. 1499–1507, 1997.
Molecular Endocrinology, vol. 11, No. 13, pp. 1961–1970, 1997.
Takeyama, K., et al., Science, vol. 277, "25–Hydroxyvitamin D3 1 alpha–hydroxylase and vitamin D synthesis", pp. 1827–1830, 1997.*
St–Arnaud, R., et al., Journal of Bone and Mineral Research, vol. 12, "The 25–hydroxyvitamin D 1–alpha–hydrolylase gene maps to the pseudovitamin D–deficiency rickets (PDDR) disease locus", pp. 1552–1559, 1997.*
Monkawa, T., et al., Biochemical and Biophysical Research Communications, vol. 239, "Molecular cloning of cDNA and genomic DNA for human 25–hydroxyvitamin D3 1alpha–hydroxylase", pp. 527–533, 1997.*

* cited by examiner

SEQUENCE LISTING

<160> NUMBER OF SEQ ID NOS: 9

<210> SEQ ID NO 1
<211> LENGTH: 501
<212> TYPE: PRT
<213> ORGANISM: Rat

<400> SEQUENCE: 1

```
Met Thr Gln Ala Val Lys Leu Ala Ser Arg Val Phe His Arg Val Gln
 1               5                  10                  15

Leu Pro Ser Gln Leu Gly Ser Asp Ser Val Leu Arg Ser Leu Ser Asp
             20                  25                  30

Ile Pro Gly Pro Ser Thr Pro Ser Phe Leu Ala Glu Leu Phe Cys Lys
         35                  40                  45

Gly Gly Leu Ser Arg Leu His Glu Leu Gln Val His Gly Ala Ala Arg
     50                  55                  60

Tyr Gly Pro Ile Trp Ser Gly Ser Phe Gly Thr Leu Arg Thr Val Tyr
 65                  70                  75                  80

Val Ala Asp Pro Ala Leu Val Glu Gln Leu Leu Arg Gln Glu Ser His
             85                  90                  95

Cys Pro Glu Arg Cys Ser Phe Ser Ser Trp Ser Glu His Arg Arg Arg
            100                 105                 110

His Gln Arg Ala Cys Gly Leu Leu Thr Ala Asp Gly Glu Glu Trp Gln
        115                 120                 125

Arg Leu Arg Ser Leu Leu Ala Pro Leu Leu Leu Arg Pro Gln Ala Ala
    130                 135                 140
```

-continued

```
Ala Gly Tyr Ala Gly Thr Leu Asp Ser Val Val Ser Asp Leu Val Arg
145                 150                 155                 160

Arg Leu Arg Arg Gln Arg Gly Arg Gly Ser Gly Leu Pro Asp Leu Val
                165                 170                 175

Leu Asp Val Ala Gly Glu Phe Tyr Lys Phe Gly Leu Glu Gly Ile Gly
            180                 185                 190

Ala Val Leu Leu Gly Ser Arg Leu Gly Cys Leu Glu Ala Glu Val Pro
        195                 200                 205

Pro Asp Thr Glu Thr Phe Ile Glu Ala Val Gly Ser Val Phe Val Ser
    210                 215                 220

Thr Leu Leu Thr Met Ala Met Pro Ser Trp Leu His Arg Leu Ile Pro
225                 230                 235                 240

Gly Pro Trp Ala Arg Leu Cys Arg Asp Trp Asp Gln Met Phe Ala Phe
                245                 250                 255

Ala Gln Lys His Val Glu Gln Arg Glu Gly Glu Ala Ala Val Arg Asn
            260                 265                 270

Gln Gly Lys Pro Glu Glu Asp Leu Pro Thr Gly His His Leu Thr His
        275                 280                 285

Phe Leu Phe Arg Glu Lys Val Ser Val Gln Ser Ile Val Gly Asn Val
    290                 295                 300

Thr Glu Leu Leu Leu Ala Gly Val Asp Thr Val Ser Asn Thr Leu Ser
305                 310                 315                 320

Trp Ala Leu Tyr Glu Leu Ser Arg His Pro Glu Val Gln Ser Ala Leu
                325                 330                 335

His Ser Glu Ile Thr Gly Ala Val Asn Pro Gly Ser Tyr Ala His Leu
            340                 345                 350

Gln Ala Thr Ala Leu Ser Gln Leu Pro Leu Leu Lys Ala Val Ile Lys
        355                 360                 365

Glu Val Leu Arg Leu Tyr Pro Val Val Pro Gly Asn Ser Arg Val Pro
    370                 375                 380

Asp Arg Asp Ile Cys Val Gly Asn Tyr Val Ile Pro Gln Asp Thr Leu
385                 390                 395                 400

Val Ser Leu Cys His Tyr Ala Thr Ser Arg Asp Pro Ala Gln Phe Arg
                405                 410                 415

Glu Pro Asn Ser Phe Asn Pro Ala Arg Trp Leu Gly Glu Gly Pro Ala
            420                 425                 430

Pro His Pro Phe Ala Ser Leu Pro Phe Gly Phe Gly Lys Arg Ser Cys
        435                 440                 445

Ile Gly Arg Arg Leu Ala Glu Leu Glu Leu Gln Met Ala Leu Ala Gln
    450                 455                 460

Ile Leu Thr His Phe Glu Val Leu Pro Glu Pro Gly Ala Leu Pro Val
465                 470                 475                 480

Lys Pro Met Thr Arg Thr Val Leu Val Pro Glu Arg Ser Ile His Leu
                485                 490                 495

Gln Phe Val Asp Arg
            500
```

<210> SEQ ID NO 2
<211> LENGTH: 508
<212> TYPE: PRT
<213> ORGANISM: human

<400> SEQUENCE: 2

```
Met Thr Gln Thr Leu Lys Tyr Ala Ser Arg Val Phe His Arg Val Arg
  1               5                  10                  15
```

```
Trp Ala Pro Glu Leu Gly Ala Ser Leu Gly Tyr Arg Glu Tyr His Ser
            20                  25                  30

Ala Arg Arg Ser Leu Ala Asp Ile Pro Gly Pro Ser Thr Pro Ser Phe
        35                  40                  45

Leu Ala Glu Leu Phe Cys Lys Gly Gly Leu Ser Arg Leu His Glu Leu
    50                  55                  60

Gln Val Gln Gly Ala Ala His Phe Gly Pro Val Trp Leu Ala Ser Phe
65                  70                  75                  80

Gly Thr Val Arg Thr Val Tyr Val Ala Pro Ala Leu Val Glu Glu
                85                  90                  95

Leu Leu Arg Gln Glu Gly Pro Arg Pro Glu Arg Cys Ser Phe Ser Pro
            100                 105                 110

Trp Thr Glu His Arg Arg Cys Arg Gln Arg Ala Cys Gly Leu Leu Thr
        115                 120                 125

Ala Glu Gly Glu Glu Trp Gln Arg Leu Arg Ser Leu Leu Ala Pro Leu
    130                 135                 140

Leu Leu Arg Pro Gln Ala Ala Arg Tyr Ala Gly Thr Leu Asn Asn
145                 150                 155                 160

Val Val Cys Asp Leu Val Arg Arg Leu Arg Arg Gln Arg Gly Arg Gly
                165                 170                 175

Thr Gly Pro Pro Ala Leu Val Arg Asp Val Ala Gly Glu Phe Tyr Lys
            180                 185                 190

Phe Gly Leu Glu Gly Ile Ala Ala Val Leu Leu Gly Ser Arg Leu Gly
        195                 200                 205

Cys Leu Glu Ala Gln Val Pro Pro Asp Thr Glu Thr Phe Ile Arg Ala
    210                 215                 220

Val Gly Ser Val Phe Val Ser Thr Leu Leu Thr Met Ala Met Pro His
225                 230                 235                 240

Trp Leu Arg His Leu Val Pro Gly Pro Trp Gly Arg Leu Cys Arg Asp
                245                 250                 255

Trp Asp Gln Met Phe Ala Phe Ala Gln Arg His Val Glu Arg Arg Glu
            260                 265                 270

Ala Glu Ala Ala Met Arg Asn Gly Gly Gln Pro Glu Lys Asp Leu Glu
        275                 280                 285

Ser Gly Ala His Leu Thr His Phe Leu Phe Arg Glu Glu Leu Pro Ala
    290                 295                 300

Gln Ser Ile Leu Gly Asn Val Thr Glu Leu Leu Leu Ala Gly Val Asp
305                 310                 315                 320

Thr Val Ser Asn Thr Leu Ser Trp Ala Leu Tyr Glu Leu Ser Arg His
                325                 330                 335

Pro Glu Val Gln Thr Ala Leu His Ser Glu Ile Thr Ala Ala Leu Ser
            340                 345                 350

Pro Gly Ser Ser Ala Tyr Pro Ser Ala Thr Val Leu Ser Gln Leu Pro
        355                 360                 365

Leu Leu Lys Ala Val Val Lys Glu Val Leu Arg Leu Tyr Pro Val Val
    370                 375                 380

Pro Gly Asn Ser Arg Val Pro Asp Lys Asp Ile His Val Gly Asp Tyr
385                 390                 395                 400

Ile Ile Pro Lys Asn Thr Leu Val Thr Leu Cys His Tyr Ala Thr Ser
                405                 410                 415

Arg Asp Pro Ala Gln Phe Pro Glu Pro Asn Ser Phe Arg Pro Ala Arg
            420                 425                 430
```

-continued

```
Trp Leu Gly Glu Gly Pro Thr Pro His Pro Phe Ala Ser Leu Pro Phe
            435                 440                 445

Gly Phe Gly Lys Arg Ser Cys Met Gly Arg Arg Leu Ala Glu Leu Glu
        450                 455                 460

Leu Gln Met Ala Leu Ala Gln Ile Leu Thr His Phe Glu Val Gln Pro
465                 470                 475                 480

Glu Pro Gly Ala Ala Pro Val Arg Pro Lys Thr Arg Thr Val Leu Val
                485                 490                 495

Pro Glu Arg Ser Ile Asn Leu Gln Phe Leu Asp Arg
            500                 505

<210> SEQ ID NO 3
<211> LENGTH: 1503
<212> TYPE: DNA
<213> ORGANISM: Rat
<220> FEATURE:
<221> NAME/KEY: CDS
<222> LOCATION: (1)..(1503)

<400> SEQUENCE: 3 atg acc cag gca gtc aag ctc gcc tcc aga gtc ttc cat cga gtc caa      48
Met Thr Gln Ala Val Lys Leu Ala Ser Arg Val Phe His Arg Val Gln
 1               5                  10                  15 ctg cct tct cag ctg ggc agt gac tcg gtt ctc cgg agt tta tct gat      96
Leu Pro Ser Gln Leu Gly Ser Asp Ser Val Leu Arg Ser Leu Ser Asp
            20                  25                  30 atc cct ggg ccc tct aca cct agc ttc ctg gct gaa ctc ttc tgc aaa     144
Ile Pro Gly Pro Ser Thr Pro Ser Phe Leu Ala Glu Leu Phe Cys Lys
        35                  40                  45 ggg ggg ctg tcc agg cta cat gaa ctg cag gtg cat ggc gct gcg cgg     192
Gly Gly Leu Ser Arg Leu His Glu Leu Gln Val His Gly Ala Ala Arg
    50                  55                  60 tac ggg cca ata tgg tcc ggc agc ttc ggg aca ctt cgc aca gtt tat     240
Tyr Gly Pro Ile Trp Ser Gly Ser Phe Gly Thr Leu Arg Thr Val Tyr
65                  70                  75                  80 gtg gcc gac cct gca ctt gta gag cag ctc ctg cga caa gaa agt cat     288
Val Ala Asp Pro Ala Leu Val Glu Gln Leu Leu Arg Gln Glu Ser His
                85                  90                  95 tgt cca gag cgc tgt agt ttc tca tct tgg tca gag cac cgt cgc cgc     336
Cys Pro Glu Arg Cys Ser Phe Ser Ser Trp Ser Glu His Arg Arg Arg
            100                 105                 110 cac cag cgg gct tgc ggg ttg cta acg gcg gat ggt gaa gaa tgg cag     384
His Gln Arg Ala Cys Gly Leu Leu Thr Ala Asp Gly Glu Glu Trp Gln
        115                 120                 125 agg ctc cga agt ctc ctg gcc ccg cta ctc ctc cga cct caa gca gcc     432
Arg Leu Arg Ser Leu Leu Ala Pro Leu Leu Leu Arg Pro Gln Ala Ala
    130                 135                 140 gcc ggc tat gct gga act ctg gac agc gtg gtc agt gac ctc gtg cga     480
Ala Gly Tyr Ala Gly Thr Leu Asp Ser Val Val Ser Asp Leu Val Arg
145                 150                 155                 160 cga cta agg cgc cag cgg gga cgt ggc tct ggg cta ccg gac cta gtt     528
Arg Leu Arg Arg Gln Arg Gly Arg Gly Ser Gly Leu Pro Asp Leu Val
                165                 170                 175 ctg gac gtg gcg gga gag ttt tac aaa ttt ggc cta gaa ggc ata ggc     576
Leu Asp Val Ala Gly Glu Phe Tyr Lys Phe Gly Leu Glu Gly Ile Gly
            180                 185                 190 gcg gtg ctg ctg gga tcg cgc ctg ggc tgc ctg gag gct gaa gtt cct     624
Ala Val Leu Leu Gly Ser Arg Leu Gly Cys Leu Glu Ala Glu Val Pro
        195                 200                 205 ccc gac aca gaa acc ttc att gag gcc gtg ggc tcg gtg ttt gtg tct     672
```

```
                                                                  -continued Pro Asp Thr Glu Thr Phe Ile Glu Ala Val Gly Ser Val Phe Val Ser
    210                 215                 220 aca ctc ttg acc atg gca atg ccc agt tgg ctg cac cgc ctt ata ccc    720
Thr Leu Leu Thr Met Ala Met Pro Ser Trp Leu His Arg Leu Ile Pro
225                 230                 235                 240 gga ccc tgg gcc cgc ctc tgc aga gac tgg gat cag atg ttt gcc ttt    768
Gly Pro Trp Ala Arg Leu Cys Arg Asp Trp Asp Gln Met Phe Ala Phe
                245                 250                 255 gcc cag aag cac gtg gag cag cgc gaa ggc gaa gct gcc gtg agg aac    816
Ala Gln Lys His Val Glu Gln Arg Glu Gly Glu Ala Ala Val Arg Asn
            260                 265                 270 cag gga aag cct gag gag gat ttg cca acg ggg cat cac tta acc cac    864
Gln Gly Lys Pro Glu Glu Asp Leu Pro Thr Gly His His Leu Thr His
        275                 280                 285 ttc ctt ttt cgg gaa aag gtg tct gtc cag tcc ata gtg gga aat gtg    912
Phe Leu Phe Arg Glu Lys Val Ser Val Gln Ser Ile Val Gly Asn Val
    290                 295                 300 aca gag cta cta ctg gct gga gtg gac acg gta tcc aat acg ctc tcc    960
Thr Glu Leu Leu Leu Ala Gly Val Asp Thr Val Ser Asn Thr Leu Ser
305                 310                 315                 320 tgg gca ctc tat gag ctc tcc cgg cac ccg gaa gtc cag tct gca ctc   1008
Trp Ala Leu Tyr Glu Leu Ser Arg His Pro Glu Val Gln Ser Ala Leu
                325                 330                 335 cac tct gag atc aca ggc gct gtg aac cct ggc tcc tat gcc cac ctc   1056
His Ser Glu Ile Thr Gly Ala Val Asn Pro Gly Ser Tyr Ala His Leu
            340                 345                 350 caa gcc act gct ctg tcc cag cta ccc ctg cta aag gct gtg atc aaa   1104
Gln Ala Thr Ala Leu Ser Gln Leu Pro Leu Leu Lys Ala Val Ile Lys
        355                 360                 365 gaa gtg ttg aga ttg tac cct gtg gta cct ggg aac tcc cgt gtc cca   1152
Glu Val Leu Arg Leu Tyr Pro Val Val Pro Gly Asn Ser Arg Val Pro
    370                 375                 380 gac aga gac atc tgt gta gga aac tat gtt att ccc caa gat aca ctg   1200
Asp Arg Asp Ile Cys Val Gly Asn Tyr Val Ile Pro Gln Asp Thr Leu
385                 390                 395                 400 gtt tcc ctc tgt cac tat gcc act tca agg gac ccc gcc cag ttt cgg   1248
Val Ser Leu Cys His Tyr Ala Thr Ser Arg Asp Pro Ala Gln Phe Arg
                405                 410                 415 gaa ccc aac tct ttt aat cca gct cga tgg ctt gga gag ggt cca gcc   1296
Glu Pro Asn Ser Phe Asn Pro Ala Arg Trp Leu Gly Glu Gly Pro Ala
            420                 425                 430 ccc cac cca ttt gca tct ctt cct ttt ggc ttt ggc aaa cga agt tgc   1344
Pro His Pro Phe Ala Ser Leu Pro Phe Gly Phe Gly Lys Arg Ser Cys
        435                 440                 445 ata ggg aga cgc ttg gca gag ctc gag cta caa atg gcg ttg gcc cag   1392
Ile Gly Arg Arg Leu Ala Glu Leu Glu Leu Gln Met Ala Leu Ala Gln
450                 455                 460 atc ttg acc cat ttt gag gtg ctg cct gag cca ggt gct ctt cca gtc   1440
Ile Leu Thr His Phe Glu Val Leu Pro Glu Pro Gly Ala Leu Pro Val
465                 470                 475                 480 aaa ccc atg acc cgg act gtc ctg gta cct gag agg agc atc cat ctc   1488
Lys Pro Met Thr Arg Thr Val Leu Val Pro Glu Arg Ser Ile His Leu
                485                 490                 495 cag ttt gta gac aga                                               1503
Gln Phe Val Asp Arg
                500

<210> SEQ ID NO 4
<211> LENGTH: 1524
<212> TYPE: DNA
```

```
<213> ORGANISM: human
<220> FEATURE:
<221> NAME/KEY: CDS
<222> LOCATION: (1)..(1524)

<400> SEQUENCE: 4 atg acc cag acc ctc aag tac gcc tcc aga gtg ttc cat cgc gtc cgc      48
Met Thr Gln Thr Leu Lys Tyr Ala Ser Arg Val Phe His Arg Val Arg
  1               5                  10                  15 tgg gcg ccc gag ttg ggc gcc tcc cta ggc tac cga gag tac cac tca      96
Trp Ala Pro Glu Leu Gly Ala Ser Leu Gly Tyr Arg Glu Tyr His Ser
             20                  25                  30 gca cgc cgg agc ttg gca gac atc cca ggc ccc tct acg ccc agc ttt     144
Ala Arg Arg Ser Leu Ala Asp Ile Pro Gly Pro Ser Thr Pro Ser Phe
         35                  40                  45 ctg gcc gaa ctt ttc tgc aag ggg ggg ctg tcg agg cta cac gag ctg     192
Leu Ala Glu Leu Phe Cys Lys Gly Gly Leu Ser Arg Leu His Glu Leu
     50                  55                  60 cag gtg cag ggc gcc gcg cac ttc ggg ccg gtg tgg cta gcc agc ttt     240
Gln Val Gln Gly Ala Ala His Phe Gly Pro Val Trp Leu Ala Ser Phe
 65                  70                  75                  80 ggg aca gtg cgc acc gtg tac gtg gct gcc cct gca ctc gtc gag gag     288
Gly Thr Val Arg Thr Val Tyr Val Ala Ala Pro Ala Leu Val Glu Glu
                 85                  90                  95 ctg ctg cga cag gag gga ccc cgg ccc gag cgc tgc agc ttc tcg ccc     336
Leu Leu Arg Gln Glu Gly Pro Arg Pro Glu Arg Cys Ser Phe Ser Pro
            100                 105                 110 tgg acg gag cac cgc cgc tgc cgc cag cgg gct tgc gga ctg ctc act     384
Trp Thr Glu His Arg Arg Cys Arg Gln Arg Ala Cys Gly Leu Leu Thr
        115                 120                 125 gcg gaa ggc gaa gaa tgg caa agg ctc cgc agt ctc ctg gcc ccg ctc     432
Ala Glu Gly Glu Glu Trp Gln Arg Leu Arg Ser Leu Leu Ala Pro Leu
    130                 135                 140 ctc ctc cgg cct caa gcg gcc gcc cgc tac gcc gga acc ctg aac aac     480
Leu Leu Arg Pro Gln Ala Ala Ala Arg Tyr Ala Gly Thr Leu Asn Asn
145                 150                 155                 160 gta gtc tgc gac ctt gtg cgg cgt ctg agg cgc cag cgg gga cgt ggc     528
Val Val Cys Asp Leu Val Arg Arg Leu Arg Arg Gln Arg Gly Arg Gly
                165                 170                 175 acg ggg ccg ccc gcc ctg gtt cgg gac gtg gcg ggg gaa ttt tac aag     576
Thr Gly Pro Pro Ala Leu Val Arg Asp Val Ala Gly Glu Phe Tyr Lys
            180                 185                 190 ttc gga ctg gaa ggc atc gcc gcg gtt ctg ctc ggc tcg cgc ttg ggc     624
Phe Gly Leu Glu Gly Ile Ala Ala Val Leu Leu Gly Ser Arg Leu Gly
        195                 200                 205 tgc ctg gag gct caa gtg cca ccc gac acg gag acc ttc atc cgc gct     672
Cys Leu Glu Ala Gln Val Pro Pro Asp Thr Glu Thr Phe Ile Arg Ala
    210                 215                 220 gtg ggc tcg gtg ttt gtg tcc acg ctg ttg acc atg gcg atg ccc cac     720
Val Gly Ser Val Phe Val Ser Thr Leu Leu Thr Met Ala Met Pro His
225                 230                 235                 240 tgg ctg cgc cac ctt gtg cct ggg ccc tgg ggc cgc ctc tgc cga gac     768
Trp Leu Arg His Leu Val Pro Gly Pro Trp Gly Arg Leu Cys Arg Asp
                245                 250                 255 tgg gac cag atg ttt gca ttt gct cag agg cac gtg gag cgg cga gag     816
Trp Asp Gln Met Phe Ala Phe Ala Gln Arg His Val Glu Arg Arg Glu
            260                 265                 270 gca gag gca gcc atg agg aac gga gga cag ccc gag aag gac ctg gag     864
Ala Glu Ala Ala Met Arg Asn Gly Gly Gln Pro Glu Lys Asp Leu Glu
        275                 280                 285
```

```
tct ggg gcg cac ctg acc cac ttc ctg ttc cgg gaa gag ttg cct gcc      912
Ser Gly Ala His Leu Thr His Phe Leu Phe Arg Glu Glu Leu Pro Ala
    290                 295                 300 cag tcc atc ctg gga aat gtg aca gag ttg cta ttg gcg gga gtg gac      960
Gln Ser Ile Leu Gly Asn Val Thr Glu Leu Leu Leu Ala Gly Val Asp
305                 310                 315                 320 acg gtg tcc aac acg ctc tct tgg gct ctg tat gag ctc tcc cgg cac     1008
Thr Val Ser Asn Thr Leu Ser Trp Ala Leu Tyr Glu Leu Ser Arg His
                325                 330                 335 ccc gaa gtc cag aca gca ctc cac tca gag atc aca gct gcc ctg agc     1056
Pro Glu Val Gln Thr Ala Leu His Ser Glu Ile Thr Ala Ala Leu Ser
            340                 345                 350 cct ggc tcc agt gcc tac ccc tca gcc act gtt ctg tcc cag ctg ccc     1104
Pro Gly Ser Ser Ala Tyr Pro Ser Ala Thr Val Leu Ser Gln Leu Pro
        355                 360                 365 ctg ctg aag gcg gtg gtc aag gaa gtg cta aga ctg tac cct gtg gta     1152
Leu Leu Lys Ala Val Val Lys Glu Val Leu Arg Leu Tyr Pro Val Val
    370                 375                 380 cct gga aat tct cgt gtc cca gac aaa gac att cat gtg ggt gac tat     1200
Pro Gly Asn Ser Arg Val Pro Asp Lys Asp Ile His Val Gly Asp Tyr
385                 390                 395                 400 att atc ccc aaa aat acg ctg gtc act ctg tgt cac tat gcc act tca     1248
Ile Ile Pro Lys Asn Thr Leu Val Thr Leu Cys His Tyr Ala Thr Ser
                405                 410                 415 agg gac cct gcc cag ttc cca gag cca aat tct ttt cgt cca gct cgc     1296
Arg Asp Pro Ala Gln Phe Pro Glu Pro Asn Ser Phe Arg Pro Ala Arg
            420                 425                 430 tgg ctg ggg gag ggt ccc acc ccc cac cca ttt gca tct ctt ccc ttt     1344
Trp Leu Gly Glu Gly Pro Thr Pro His Pro Phe Ala Ser Leu Pro Phe
        435                 440                 445 ggc ttt ggc aag cgc agc tgt atg ggg aga cgc ctg gca gag ctt gaa     1392
Gly Phe Gly Lys Arg Ser Cys Met Gly Arg Arg Leu Ala Glu Leu Glu
    450                 455                 460 ttg caa atg gct ttg gcc cag atc cta aca cat ttt gag gtg cag cct     1440
Leu Gln Met Ala Leu Ala Gln Ile Leu Thr His Phe Glu Val Gln Pro
465                 470                 475                 480 gag cca ggt gcg gcc cca gtt aga ccc aag acc cgg act gtc ctg gta     1488
Glu Pro Gly Ala Ala Pro Val Arg Pro Lys Thr Arg Thr Val Leu Val
                485                 490                 495 cct gaa agg agc atc aac cta cag ttt ttg gac aga                     1524
Pro Glu Arg Ser Ile Asn Leu Gln Phe Leu Asp Arg
            500                 505

<210> SEQ ID NO 5
<211> LENGTH: 2469
<212> TYPE: DNA
<213> ORGANISM: Rat
<220> FEATURE:
<221> NAME/KEY: CDS
<222> LOCATION: (24)..(1526)

<400> SEQUENCE: 5
gagcagactc ctcaaacaca aac atg acc cag gca gtc aag ctc gcc tcc aga     53
                        Met Thr Gln Ala Val Lys Leu Ala Ser Arg
                          1               5                  10 gtc ttc cat cga gtc caa ctg cct tct cag ctg ggc agt gac tcg gtt      101
Val Phe His Arg Val Gln Leu Pro Ser Gln Leu Gly Ser Asp Ser Val
             15                  20                  25 ctc cgg agt tta tct gat atc cct ggg ccc tct aca cct agc ttc ctg     149
Leu Arg Ser Leu Ser Asp Ile Pro Gly Pro Ser Thr Pro Ser Phe Leu
         30                  35                  40
```

-continued

| | |
|---|---|
| gct gaa ctc ttc tgc aaa ggg ggg ctg tcc agg cta cat gaa ctg cag<br>Ala Glu Leu Phe Cys Lys Gly Gly Leu Ser Arg Leu His Glu Leu Gln<br>         45                     50                 55 | 197 |
| gtg cat ggc gct gcg cgg tac ggg cca ata tgg tcc ggc agc ttc ggg<br>Val His Gly Ala Ala Arg Tyr Gly Pro Ile Trp Ser Gly Ser Phe Gly<br>60                      65                     70 | 245 |
| aca ctt cgc aca gtt tat gtg gcc gac cct gca ctt gta gag cag ctc<br>Thr Leu Arg Thr Val Tyr Val Ala Asp Pro Ala Leu Val Glu Gln Leu<br>75                      80               85                     90 | 293 |
| ctg cga caa gaa agt cat tgt cca gag cgc tgt agt ttc tca tct tgg<br>Leu Arg Gln Glu Ser His Cys Pro Glu Arg Cys Ser Phe Ser Ser Trp<br>                   95                    100              105 | 341 |
| tca gag cac cgt cgc cgc cac cag cgg gct tgc ggg ttg cta acg gcg<br>Ser Glu His Arg Arg Arg His Gln Arg Ala Cys Gly Leu Leu Thr Ala<br>          110                        115                      120 | 389 |
| gat ggt gaa gaa tgg cag agg ctc cga agt ctc ctg gcc ccg cta ctc<br>Asp Gly Glu Glu Trp Gln Arg Leu Arg Ser Leu Leu Ala Pro Leu Leu<br>                125                      130                  135 | 437 |
| ctc cga cct caa gca gcc gcc ggc tat gct gga act ctg gac agc gtg<br>Leu Arg Pro Gln Ala Ala Ala Gly Tyr Ala Gly Thr Leu Asp Ser Val<br>140                     145                      150 | 485 |
| gtc agt gac ctc gtg cga cga cta agg cgc cag cgg gga cgt ggc tct<br>Val Ser Asp Leu Val Arg Arg Leu Arg Arg Gln Arg Gly Arg Gly Ser<br>155                     160                      165                  170 | 533 |
| ggg cta ccg gac cta gtt ctg gac gtg gcg gga gag ttt tac aaa ttt<br>Gly Leu Pro Asp Leu Val Leu Asp Val Ala Gly Glu Phe Tyr Lys Phe<br>                      175                      180                  185 | 581 |
| ggc cta gaa ggc ata ggc gcg gtg ctg ctg gga tcg cgc ctg ggc tgc<br>Gly Leu Glu Gly Ile Gly Ala Val Leu Leu Gly Ser Arg Leu Gly Cys<br>          190                        195                      200 | 629 |
| ctg gag gct gaa gtt cct ccc gac aca gaa acc ttc att gag gcc gtg<br>Leu Glu Ala Glu Val Pro Pro Asp Thr Glu Thr Phe Ile Glu Ala Val<br>                205                      210                  215 | 677 |
| ggc tcg gtg ttt gtg tct aca ctc ttg acc atg gca atg ccc agt tgg<br>Gly Ser Val Phe Val Ser Thr Leu Leu Thr Met Ala Met Pro Ser Trp<br>220                     225                      230 | 725 |
| ctg cac cgc ctt ata ccc gga ccc tgg gcc cgc ctc tgc aga gac tgg<br>Leu His Arg Leu Ile Pro Gly Pro Trp Ala Arg Leu Cys Arg Asp Trp<br>235                     240                      245                  250 | 773 |
| gat cag atg ttt gcc ttt gcc cag aag cac gtg gag cag cgc gaa ggc<br>Asp Gln Met Phe Ala Phe Ala Gln Lys His Val Glu Gln Arg Glu Gly<br>                255                      260                  265 | 821 |
| gaa gct gcc gtg agg aac cag gga aag cct gag gag gat ttg cca acg<br>Glu Ala Ala Val Arg Asn Gln Gly Lys Pro Glu Glu Asp Leu Pro Thr<br>270                     275                      280 | 869 |
| ggg cat cac tta acc cac ttc ctt ttt cgg gaa aag gtg tct gtc cag<br>Gly His His Leu Thr His Phe Leu Phe Arg Glu Lys Val Ser Val Gln<br>285                     290                      295 | 917 |
| tcc ata gtg gga aat gtg aca gag cta cta ctg gct gga gtg gac acg<br>Ser Ile Val Gly Asn Val Thr Glu Leu Leu Leu Ala Gly Val Asp Thr<br>300                     305                      310 | 965 |
| gta tcc aat acg ctc tcc tgg gca ctc tat gag ctc tcc cgg cac ccg<br>Val Ser Asn Thr Leu Ser Trp Ala Leu Tyr Glu Leu Ser Arg His Pro<br>315                     320                      325                  330 | 1013 |
| gaa gtc cag tct gca ctc cac tct gag atc aca ggc gct gtg aac cct<br>Glu Val Gln Ser Ala Leu His Ser Glu Ile Thr Gly Ala Val Asn Pro<br>                335                      340                  345 | 1061 |
| ggc tcc tat gcc cac ctc caa gcc act gct ctg tcc cag cta ccc ctg<br>Gly Ser Tyr Ala His Leu Gln Ala Thr Ala Leu Ser Gln Leu Pro Leu<br>350                     355                      360 | 1109 |

```
cta aag gct gtg atc aaa gaa gtg ttg aga ttg tac cct gtg gta cct      1157
Leu Lys Ala Val Ile Lys Glu Val Leu Arg Leu Tyr Pro Val Val Pro
        365                 370                 375 ggg aac tcc cgt gtc cca gac aga gac atc tgt gta gga aac tat gtt      1205
Gly Asn Ser Arg Val Pro Asp Arg Asp Ile Cys Val Gly Asn Tyr Val
    380                 385                 390 att ccc caa gat aca ctg gtt tcc ctc tgt cac tat gcc act tca agg      1253
Ile Pro Gln Asp Thr Leu Val Ser Leu Cys His Tyr Ala Thr Ser Arg
395                 400                 405                 410 gac ccc gcc cag ttt cgg gaa ccc aac tct ttt aat cca gct cga tgg      1301
Asp Pro Ala Gln Phe Arg Glu Pro Asn Ser Phe Asn Pro Ala Arg Trp
                415                 420                 425 ctt gga gag ggt cca gcc ccc cac cca ttt gca tct ctt cct ttt ggc      1349
Leu Gly Glu Gly Pro Ala Pro His Pro Phe Ala Ser Leu Pro Phe Gly
            430                 435                 440 ttt ggc aaa cga agt tgc ata ggg aga cgc ttg gca gag ctc gag cta      1397
Phe Gly Lys Arg Ser Cys Ile Gly Arg Arg Leu Ala Glu Leu Glu Leu
        445                 450                 455 caa atg gcg ttg gcc cag atc ttg acc cat ttt gag gtg ctg cct gag      1445
Gln Met Ala Leu Ala Gln Ile Leu Thr His Phe Glu Val Leu Pro Glu
    460                 465                 470 cca ggt gct ctt cca gtc aaa ccc atg acc cgg act gtc ctg gta cct      1493
Pro Gly Ala Leu Pro Val Lys Pro Met Thr Arg Thr Val Leu Val Pro
475                 480                 485                 490 gag agg agc atc cat ctc cag ttt gta gac aga tagtcctgtg gaaggcagct    1546
Glu Arg Ser Ile His Leu Gln Phe Val Asp Arg
                495                 500 gtcatcatct ctctccagac tggattttc ttactatgca caagaggcac actctccctc    1606
gaggcctgtc tgtctgagca aacttcagga agcaggcccg ggcctatctg tgcttgacct    1666
gactcagcag gtaccacaga accaggatcc tttctcctgc tcagtacctc tcctgatcat    1726
tcctcaagat ccaaagcctt cagattttaa cacatcctta aagggccaac tcgggggtta    1786
actaacagcc ccaggcagcc tgggcaggga tcccccactg atccttccat gcttacagtg    1846
ttcactgaca gctgtctaag catccattgc agcacaaact aagtgactgt gcacctggtc    1906
tgcacctggt ctgcacctgg ttgcgtctct gcctgaccat gtgagctctt tgagaagagt    1966
gatgactact gggcttttag ctcttttcct ttttgggaca cagtcttgct attgtactcc    2026
atgctgtcct tgaacccaca agccctcacc tcaccttccc aagtgttggg ttacggacat    2086
tagctatggc ttccagcttt attagtcttt ctatctcctg ccatggtcta tccccggcta    2146
tttgatacta tatattctca gattgaatct ggaccatgtg gtagaaggga tgaccactca    2206
ccaggctcta cccaccactt tatcttaatc ttttctctag gaaagtgaat ctctccttgc    2266
cttacagcat tttaaagctc cccttggctg ttctgctctt tagccactct aaagtggatc    2326
cactctactt ctcaccaccc atctttctgc accccagcct gtctttttat atttaaaaaa    2386
ttgtatttat tatgttttca aataaaatgt ttactccttg aaaaaaaaaa aaaaaaaaa    2446 aaaaaaaaa aaaaaaaaa aaa                                              2469

<210> SEQ ID NO 6
<211> LENGTH: 2469
<212> TYPE: DNA
<213> ORGANISM: human
<220> FEATURE:
<221> NAME/KEY: CDS
<222> LOCATION: (122)..(1645)

<400> SEQUENCE: 6
```

```
aggagggatt ggctgaggag cttggagagg gggcgtcatc acctcaccca aaggttaaat        60 agggggttgag atatgatgct caggagaagc gctttctttc gcgagcaccc tgaaccagac      120 c atg acc cag acc ctc aag tac gcc tcc aga gtg ttc cat cgc gtc cgc       169
  Met Thr Gln Thr Leu Lys Tyr Ala Ser Arg Val Phe His Arg Val Arg
   1               5                  10                  15 tgg gcg ccc gag ttg ggc gcc tcc cta ggc tac cga gag tac cac tca         217
Trp Ala Pro Glu Leu Gly Ala Ser Leu Gly Tyr Arg Glu Tyr His Ser
                 20                  25                  30 gca cgc cgg agc ttg gca gac atc cca ggc ccc tct acg ccc agc ttt         265
Ala Arg Arg Ser Leu Ala Asp Ile Pro Gly Pro Ser Thr Pro Ser Phe
             35                  40                  45 ctg gcc gaa ctt ttc tgc aag ggg ggg ctg tcg agg cta cac gag ctg         313
Leu Ala Glu Leu Phe Cys Lys Gly Gly Leu Ser Arg Leu His Glu Leu
     50                  55                  60 cag gtg cag ggc gcc gcg cac ttc ggg ccg gtg tgg cta gcc agc ttt         361
Gln Val Gln Gly Ala Ala His Phe Gly Pro Val Trp Leu Ala Ser Phe
 65                  70                  75                  80 ggg aca gtg cgc acc gtg tac gtg gct gcc cct gca ctc gtc gag gag         409
Gly Thr Val Arg Thr Val Tyr Val Ala Ala Pro Ala Leu Val Glu Glu
                 85                  90                  95 ctg ctg cga cag gag gga ccc cgg ccc gag cgc tgc agc ttc tcg ccc         457
Leu Leu Arg Gln Glu Gly Pro Arg Pro Glu Arg Cys Ser Phe Ser Pro
             100                 105                 110 tgg acg gag cac cgc cgc tgc cgc cag cgg gct tgc gga ctg ctc act         505
Trp Thr Glu His Arg Arg Cys Arg Gln Arg Ala Cys Gly Leu Leu Thr
     115                 120                 125 gcg gaa ggc gaa gaa tgg caa agg ctc cgc agt ctc ctg gcc ccg ctc         553
Ala Glu Gly Glu Glu Trp Gln Arg Leu Arg Ser Leu Leu Ala Pro Leu
 130                 135                 140 ctc ctc cgg cct caa gcg gcc gcc cgc tac gcc gga acc ctg aac aac         601
Leu Leu Arg Pro Gln Ala Ala Ala Arg Tyr Ala Gly Thr Leu Asn Asn
145                 150                 155                 160 gta gtc tgc gac ctt gtg cgg cgt ctg agg cgc cag cgg gga cgt ggc         649
Val Val Cys Asp Leu Val Arg Arg Leu Arg Arg Gln Arg Gly Arg Gly
                 165                 170                 175 acg ggg ccg ccc gcc ctg gtt cgg gac gtg gcg ggg gaa ttt tac aag         697
Thr Gly Pro Pro Ala Leu Val Arg Asp Val Ala Gly Glu Phe Tyr Lys
             180                 185                 190 ttc gga ctg gaa ggc atc gcc gcg gtt ctg ctc ggc tcg cgc ttg ggc         745
Phe Gly Leu Glu Gly Ile Ala Ala Val Leu Leu Gly Ser Arg Leu Gly
     195                 200                 205 tgc ctg gag gct caa gtg cca ccc gac acg gag acc ttc atc cgc gct         793
Cys Leu Glu Ala Gln Val Pro Pro Asp Thr Glu Thr Phe Ile Arg Ala
 210                 215                 220 gtg ggc tcg gtg ttt gtg tcc acg ctg ttg acc atg gcg atg ccc cac         841
Val Gly Ser Val Phe Val Ser Thr Leu Leu Thr Met Ala Met Pro His
225                 230                 235                 240 tgg ctg cgc cac ctt gtg cct ggg ccc tgg ggc cgc ctc tgc cga gac         889
Trp Leu Arg His Leu Val Pro Gly Pro Trp Gly Arg Leu Cys Arg Asp
                 245                 250                 255 tgg gac cag atg ttt gca ttt gct cag agg cac gtg gag cgg cga gag         937
Trp Asp Gln Met Phe Ala Phe Ala Gln Arg His Val Glu Arg Arg Glu
             260                 265                 270 gca gag gca gcc atg agg aac gga gga cag ccc gag aag gac ctg gag         985
Ala Glu Ala Ala Met Arg Asn Gly Gly Gln Pro Glu Lys Asp Leu Glu
     275                 280                 285 tct ggg gcg cac ctg acc cac ttc ctg ttc cgg gaa gag ttg cct gcc        1033
Ser Gly Ala His Leu Thr His Phe Leu Phe Arg Glu Glu Leu Pro Ala
```

-continued

```
             290                 295                 300
cag tcc atc ctg gga aat gtg aca gag ttg cta ttg gcg gga gtg gac    1081
Gln Ser Ile Leu Gly Asn Val Thr Glu Leu Leu Leu Ala Gly Val Asp
305                 310                 315                 320 acg gtg tcc aac acg ctc tct tgg gct ctg tat gag ctc tcc cgg cac    1129
Thr Val Ser Asn Thr Leu Ser Trp Ala Leu Tyr Glu Leu Ser Arg His
                325                 330                 335 ccc gaa gtc cag aca gca ctc cac tca gag atc aca gct gcc ctg agc    1177
Pro Glu Val Gln Thr Ala Leu His Ser Glu Ile Thr Ala Ala Leu Ser
            340                 345                 350 cct ggc tcc agt gcc tac ccc tca gcc act gtt ctg tcc cag ctg ccc    1225
Pro Gly Ser Ser Ala Tyr Pro Ser Ala Thr Val Leu Ser Gln Leu Pro
        355                 360                 365 ctg ctg aag gcg gtg gtc aag gaa gtg cta aga ctg tac cct gtg gta    1273
Leu Leu Lys Ala Val Val Lys Glu Val Leu Arg Leu Tyr Pro Val Val
370                 375                 380 cct gga aat tct cgt gtc cca gac aaa gac att cat gtg ggt gac tat    1321
Pro Gly Asn Ser Arg Val Pro Asp Lys Asp Ile His Val Gly Asp Tyr
385                 390                 395                 400 att atc ccc aaa aat acg ctg gtc act ctg tgt cac tat gcc act tca    1369
Ile Ile Pro Lys Asn Thr Leu Val Thr Leu Cys His Tyr Ala Thr Ser
                405                 410                 415 agg gac cct gcc cag ttc cca gag cca aat tct ttt cgt cca gct cgc    1417
Arg Asp Pro Ala Gln Phe Pro Glu Pro Asn Ser Phe Arg Pro Ala Arg
            420                 425                 430 tgg ctg ggg gag ggt ccc acc ccc cac cca ttt gca tct ctt ccc ttt    1465
Trp Leu Gly Glu Gly Pro Thr Pro His Pro Phe Ala Ser Leu Pro Phe
        435                 440                 445 ggc ttt ggc aag cgc agc tgt atg ggg aga cgc ctg gca gag ctt gaa    1513
Gly Phe Gly Lys Arg Ser Cys Met Gly Arg Arg Leu Ala Glu Leu Glu
450                 455                 460 ttg caa atg gct ttg gcc cag atc cta aca cat ttt gag gtg cag cct    1561
Leu Gln Met Ala Leu Ala Gln Ile Leu Thr His Phe Glu Val Gln Pro
465                 470                 475                 480 gag cca ggt gcg gcc cca gtt aga ccc aag acc cgg act gtc ctg gta    1609
Glu Pro Gly Ala Ala Pro Val Arg Pro Lys Thr Arg Thr Val Leu Val
                485                 490                 495 cct gaa agg agc atc aac cta cag ttt ttg gac aga tagtcccatg         1655
Pro Glu Arg Ser Ile Asn Leu Gln Phe Leu Asp Arg
            500                 505 gaaagagact gtcatcatca cccttctcatt catcataggg ataagatttt ttgtaggcac  1715
aagaccaagg tatacatctt ccctaatgc ctatctgacc aaactggata gaaccaccat   1775
agtgaagtgt gaggcggccc tgaccaatgt gtgaagtatg cacttggcct gactcaggaa  1835
gccaggtgag aaaaccatgg tctctctgct tgcttggccc ttctgatcat gtatgcatcc  1895 cccaaggat aaatcagatt ttaactaata atgctggatg gcctgaggaa agattcaact   1955
gcctctcttt ttgggctttc atagtgttca ttgatgctgc tggctaagca tttatcaaag  2015
cataagctca gtaactgtgc atctggtctg tacctggttg gtccttcgtc tttgcatgta  2075
agctctttga gaggaagggt gaagccttat ttgttttta tgtcccctgc cagggcctgt   2135
ctctgactag gtgtcaccat acacattctt agattgaatc tgaaccatgt ggcagaaggg  2195
ataagcagct tacttagtag gctctgtcta ccccttcct tctttgtctt gccctagga    2255 aggtgaatct gccctagcct ggtttacggt ttcttataac tctcctttgc tctctggcca  2315
ctattaagtg ggtttgcccc atcacttagt tctcaggcag agacatcttt gggcctgtcc  2375
ctgcccaggc ctctggcttt ttatattgaa aattttttaaa tattcacaaa ttttagaata 2435
```

```
aatcaaatat tccattaaaa aaaaaaaaaa aaaa                              2469

<210> SEQ ID NO 7
<211> LENGTH: 23
<212> TYPE: DNA
<213> ORGANISM: synthetic DNA

<400> SEQUENCE: 7
ctsctsaarg chgtsatyaa rga                                            23

<210> SEQ ID NO 8
<211> LENGTH: 22
<212> TYPE: DNA
<213> ORGANISM: synthetic DNA

<400> SEQUENCE: 8
ckcttbccra abccraargg va                                             22

<210> SEQ ID NO 9
<211> LENGTH: 25
<212> TYPE: DNA
<213> ORGANISM: synthetic DNA

<400> SEQUENCE: 9
aaggcagtga ttaaggaagt gttga                                          25
```

25-HYDROXYVITAMIN D$_3$-1α-HYDROXYLASE AND DNA ENCODING THE HYDROXYLASE

BACKGROUND OF THE INVENTION

1. Field of the Invention

The present invention relates to a polypeptide having 25-hydroxyvitamin D$_3$-1α-hydroxylase activity, DNA encoding the polypeptide, a recombinant DNA prepared by inserting the DNA in a vector, a transformant carrying the recombinant DNA, a method for preparing 25-hydroxyvitamin D$_3$-1α-hydroxylase by using the transformant, a method for preparing 1α, 25-dihydroxyvitamin D$_3$ by using the polypeptide having 25-hydroxyvitamin D$_3$-1α-hydroxylase activity and to an antibody recognizing the polypeptide.

2. Prior Art

Active type vitamin D$_3$ has been known as a hormone having various biological actions such as the action of controlling calcium metabolism, the induction of cellular differentiation, and immunomodulation.

It has been known that active type vitamin D$_3$ is generated from vitamin D$_3$ having no biological actions through the metabolism in biological organisms.

As one of the action mechanisms of active type vitamin D$_3$ an action mechanism through cytoplasmic receptors have been known.

It has been known that active type vitamin D$_3$ is essentially 1α, 25-dihydroxyvitamin D$_3$ wherein the positions 1α and 25 have been hydroxylated. As to the metabolic pathway for the activation, it has been known that vitamin D$_3$ is firstly modified into 25-hydroxyvitamin D$_3$ by introducing a hydroxyl group into the position 25 and the position 1α of the resulting 25-hydroxyvitamin D$_3$ is hydroxylated to form 1α, 25-dihydroxyvitamin D$_3$ [All of vitamin D$_3$, edited by Etsuro Ogata, Tateo Suda, and Yosuke Ogura, Kodansha Scientific, Co. (1993)].

As 25-hydroxylase gene which functions to introduce a hydroxyl group into the position 25, a gene derived from rat liver has been cloned (Japanese Published Unexamined Patent Application No.2324893/1991). Furthermore, the gene of the hydroxylase of the position 24 of vitamin D$_3$ has been cloned [Japanese Published Unexamined Patent Application No.207196/1992].

As an enzyme to hydroxylate the position 1α of vitamin D$_3$, human CYP27 has been reported [Proc. Natl. Acad. Sci., USA, 91, 10014 (1994)], but the activity of the enzyme to hydroxylate the position 1α is a secondary activity, so the activity is very weak, which is not an essential activity. Additionally, the activity is not inducible.

It has been known that 25-hydroxyvitamin D$_3$-1α-hydroxylase activity is induced in the kidneys of rats and chickens fed with vitamin D$_3$ deficient diet [Gerontology, 42 (Supplement 1), 67–77 (1996)].

Up to now, no report has been presented in any of animal species concerning the isolation of any enzyme polypeptide catalyzing the final stage of vitamin D$_3$ activation to hydroxylate the most significant position 1α, or the isolation of a gene encoding the polypeptide.

As a method for producing 1α,25-dihydroxyvitamin D$_3$, a method comprising the use of kidney homogenates or mitochondria fractions of animals such as chicken has been known [Nature, 230, 228 (1971); J. Biol. Chem., 247, 7528 (1972); Biochemistry, 25, 5512 (1986)], but the method requires a vast amount of animal kidney or liver and demands laborious works to prepare them, so the method is insufficient and is not practical. It has been found a microorganism having activity to directly induce hydroxyl groups into the positions 1α and 25 (Japanese Published Examined Patent Application No.64678/1992), but the activity is very weak and substrate specificity is low, so it is difficult to separate the product and byproducts.

SUMMARY OF THE INVENTION

An object of the present invention is to provide a polypeptide having 25-hydroxyvitamin D$_3$-1α-hydroxylase activity and a gene encoding the polypeptide. 25-hydroxyvitamin D$_3$-1α-hydroxylase catalyzes the final stage of vitamin D$_3$ activation, and is useful for prevention, diagnosis and therapeutic treatment of diseases such as osteoporosis induced by the decrease of active type vitamin D$_3$.

The present invention relates to a polypeptide having 25-hydroxyvitamin D$_3$-1α-hydroxylase activity, DNA encoding the polypeptide, a recombinant DNA prepared by inserting the DNA in a vector, a transformant carrying the recombinant DNA, a method for producing 25-hydroxyvitamin D$_3$-1α-hydroxylase by using the transformant, a method for producing 1α, 25-dihydroxyvitamin D$_3$ by using the polypeptide having 25-hydroxyvitamin D$_3$-1α-hydroxylase activity and an antibody recognizing the polypeptide.

DETAILED DESCRIPTION OF THE INVENTION

Figure 1:
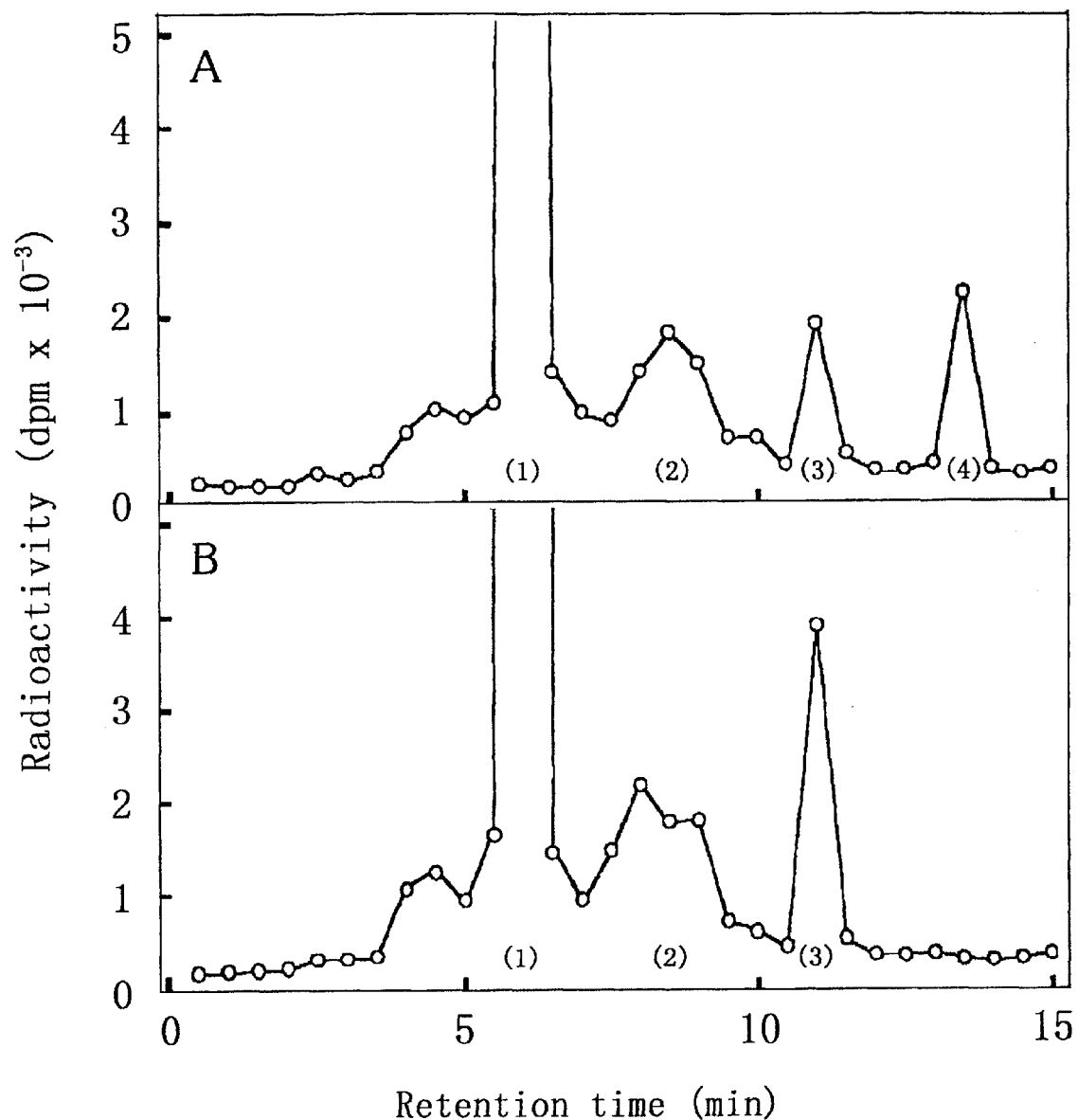
FIG. 1 is an HPLC chart of the identified vitamin D$_3$ metabolites in cells to which pcMD3R or pcDNA3 is introduced, wherein "A" shows the results of the identification of vitamin D$_3$ metabolites in the cells to which pcMD3R is introduced; and "B" represents the results of vitamin D$_3$ metabolites in the cells to which pcDNA3 is introduced, wherein (1) represents 25-hydroxyvitamin D$_3$; (2) represents 24, 25-dihydroxyvitamin D$_3$; (3) represents 10-oxo-19-nor-25-hydroxyvitamin D$_3$ and (4) represents α, 25-dihydroxyvitamin D$_3$.

The present invention will now be described in detail.

As the polypeptide of the present invention, any polypeptide having 25-hydroxyvitamin D$_3$-1α-hydroxylase activity may be used, for example including a polypeptide having an amino acid sequence selected from amino acid sequences represented by SEQ ID NOS.1 and 2, or having an amino acid sequence in which one or more amino acid residues are deleted, substituted or added in the amino acid sequence of a polypeptide, the amino acid sequence being selected from amino acid sequences represented by SEQ ID NOS.1 and 2, and having 25-hydroxyvitamin D$_3$-1α-hydroxylase activity.

The polypeptide having an amino acid sequence in which one or more amino acid residues are deleted, substituted or added in the amino acid sequence, the amino acid sequence being selected from amino acid sequences represented by SEQ ID NOS.1 and 2, and having 25-hydroxyvitamin D$_3$-1α-hydroxylase activity may be prepared according to the method described in Nucleic Acids Research, 10, 6487 (1982); Proc. Natl. Acad. Sci., USA, 79, 6409 (1982); Proc. Natl. Acad. Sci., USA, 81, 5662 (1984); Science, 224, 1431 (1984); PCT WO85/00817 (1985); Nature, 316, 601 (1985); Gene, 34, 315 (1985); Nucleic Acids Research, 13, 4431 (1985); Current Protocols in Molecular Biology, Chapter 8. Mutagenesis of Cloned DNA, John Wiley & Sons, Inc. (1989); and the like.

DNA of the present invention includes DNA encoding the polypeptide of the present invention, for example, DNA encoding the polypeptide having an amino acid sequence selected from amino acid sequences represented by SEQ ID NOS.1 and 2, DNA encoding the polypeptide having an amino acid sequence in which one or more amino acid residues are deleted, substituted or added in the amino acid sequence selected from amino acid sequences represented by SEQ ID NOS.1 and 2, and having 25-hydroxyvitamin $D_3$-1α-hydroxylase activity, DNA comprising a nucleotide sequence selected from SEQ ID NOS.3 and 4, or DNA hybridizable with these DNAs under stringent conditions.

In the present application, "DNA hybridizable under stringent conditions" means DNA recovered by using the DNA encoding the polypeptide having 25-hydroxyvitamin $D_3$-1α-hydroxylase activity as a probe through colony hybridization, plaque hybridization or Southern blot hybridization or the like, specific example of which includes DNA identified by hybridization in the presence of 0.7 to 1.0 M NaCl at 65° C. by using a filter on which a DNA prepared from colonies or plaques is immobilized and then rinsing the filter at a condition of 65° C. by using 0.1 to 2×SSC solutions (the composition of 1×SSC solution is as follows; 150 mM NaCl and 15 mM sodium citrate).

The hybridization can be carried out according to the method described in Molecular Cloning, A Laboratory Manual, 2-nd edition, Sambrook, Fritsch & Maniatis, eds., Cold Spring Harbor Laboratory Press (1989) (referred to as "Molecular Cloning, 2-nd edition" hereinafter), Current Protocols in Molecular Biology, Supplement 1 to 34, DNA Cloning 1: Core Techniques, A Practical Approach, Second Edition, Oxford University (1995) or the like. Hybridizable DNA includes for example DNA having homology of 60% or more, preferably 80% or more, more preferably 95% or more to the nucleotide sequence of the DNA encoding the polypeptide having an amino acid sequence selected from amino acid sequences represented by SEQ ID NOS.1 and 2.

The antibody of the present invention includes antibodies recognizing the polypeptide described above.

MODE FOR CARRYING OUT THE INVENTION

The present invention will now be described in detail below.

1) Preparation of cDNA Library From mRNA Derived From Rat Kidney

From tissues, for example kidney of a rat fed with vitamin $D_3$ deficient diet to induce 25-hydroxyvitamin $D_3$-1α-hydroxylase activity, mRNA [sometimes referred to as poly(A)$^+$RNA] is prepared.

Method for preparing such mRNA includes a method comprising preparing the whole RNA from the rat tissues and preparing then mRNA as poly(A)$^+$RNA by using the oligo (dT) immobilized cellulose column method [Molecular Cloning, 2-nd edition]; a method comprising directly preparing mRNA from rat tissues by using kits such as Fast Track mRNA Isolation kit manufactured by Invitrogen, Co, and Quick Prep mRNA Purification Kit, manufactured by Pharmacia, Co. and the like.

Method for preparing the whole RNA includes thiocyanate guanidine-trifluoroacetic acid cesium method [Methods in Enzymol., 154, 3 (1987)], AGPC method [Experimental Medicine, 9, 1937 (1991)] and the like.

The whole RNA and mRNA may be prepared from rat tissues with no induction of 25-hydroxyvitamin $D_3$-1α-hydroxylase activity by similar method described above.

By using the mRNA prepared above, a cDNA library is prepared by a conventional method.

Method for preparing the cDNA library includes for example a method for preparing a cDNA library, comprising synthesizing cDNA from the mRNA derived from the kidney resected from a rat with 25-hydroxyvitamin $D_3$-1α-hydroxylase activity induced, by using ZAP-cDNA synthesis kit manufactured by Stratagene, Co., cDNA Synthesis System manufactured by GIBCO BRL, Co. and the like, ligating then an adapter with a digestible site with an appropriate restriction enzyme, digesting a cloning vector λ ZAP II with the restriction enzyme, and inserting the cDNA into the digested site of the cloning vector.

As the cloning vector to prepare the cDNA library, any cloning vector capable of autonomously replicating in *Escherichia coli* K12 may be used.

The cloning vector includes for example phage vector, plasmid vector and the like, preferably including λ ZAP II described above, in addition to pUC18, pBluescript (Stratagene, Co.) and the like.

As a host microorganism, any microorganism of species *Escherichia coli* may be used, preferably including *Escherichia coli* XL1-Blue, *Escherichia coli* XL2-Blue, *Escherichia coli* DH1, *Escherichia coli* MC1000 and the like.

2) Selection of an Amino Acid Sequence Characteristic to Vitamin $D_3$ Hydroxylase Screening a region with the amino acid sequence present in common with both the hydroxylase of the position 25 of rat vitamin $D_3$ [Japanese Published Unexamined Patent Application No.232493/1991] and the hydroxylase of the position 24 thereof (Japanese Published Unexamined Patent Application No.207196/1992), the amino acid sequence present in the region is selected as the amino acid sequence characteristic to the hydroxylase of vitamin $D_3$.

The region with the amino acid sequence includes for example adrenodoxin binding region (referred to as "Region A" hereinafter), heme binding region (referred to as "Region H" hereinafter) and the like.

3) Amplification of a Partial Fragment of DNA Encoding 25-hydroxyvitamin $D_3$-1α-hydroxylase Based on the amino acid sequence of the region selected in 2) above and with reference to the codons of rat, a sense primer and an antisense primer are designed and prepared, which are appropriate for the amplification of the DNA encoding 25-hydroxyvitamin $D_3$-1α-hydroxylase by polymerase chain reaction (referred to as "PCR" hereinafter).

Such primers include DNA comprising a nucleotide sequence selected from nucleotide sequences represented by SEQ ID NOS.7, 8 and 9.

Using the mRNA recovered in 1), first strand DNA is synthesized by reverse transcriptase reaction. DNA synthesis may be carried out using a cDNA synthetic kit manufactured by Stratagene, Co.

Using the first strand DNA as a template and utilizing the sense primers and antisense primers as prepared above, RT (reverse transcription)-PCR is carried out to amplify a DNA region containing a part of DNA encoding 25-hydroxyvitamin $D_3$-1α-hydroxylase.

Using the RT-PCR amplified fragments and 3' RACE system kit manufactured by BRL, Co., PCR amplification is carried out between the RT-PCR amplified fragment and the 3-terminal poly(A) structure to recover a longer PCR amplified fragment additionally containing the noncoding region on 3' side.

More specifically, a PCR amplified fragment containing the 3' noncoding region can be recovered by synthesizing cDNA using the mRNA recovered in 1) and the oligo dT/AUAP primer in the 3' RACE system kit manufactured by BRL, CO. and conducting PCR amplification using the DNA as a template and using the AUAP primer in the 3' RACE system kit manufactured by BRL and the RT-PCR amplified fragment.

Using 5' RACE method in the same manner, a PCR amplified fragment containing the 5' region can be recovered.

It can be confirmed that the amplified DNA fragment is a partial fragment of the DNA encoding 25-hydroxyvitamin $D_3$-1α-hydroxylase by the following method.

Poly(A)$^+$RNAs derived from a rat induced with 25-hydroxyvitamin $D_3$-1α-hydroxylase activity and a non-induced rat are individually subject to agarose electrophoresis, and the poly(A)$^+$RNAs electrophoresed are then individually transferred onto each membrane filter in a conventional manner.

Using these membrane filters, Northern hybridization is carried out using the amplified DNA fragment as a probe.

By confirming that the amplified DNA fragment is hybridizable only when using the membrane filter prepared from the poly(A)$^+$RNA derived from the rat induced with the activity, it is revealed that the DNA fragment is a partial fragment of the DNA encoding 25-hydroxyvitamin $D_3$-1α-hydroxylase.

The amplified DNA fragment is then inserted into a plasmid, and the resulting plasmid can be used for nucleotide sequencing and the assay of expression specificity.

The method for inserting the fragment into a plasmid includes a method for inserting the fragment into a plasmid, comprising extracting the amplified DNA fragment from the agarose using a DNA purification kit (manufactured by Bio Rad Co.) and ligating the fragment with a vector pCRII (manufactured by Invitrogen, Co.).

4) Selection of a Clone Carrying DNA Encoding 25-hydroxyvitamin $D_3$-1α-hydroxylase A cDNA library is screened by labeling the amplified DNA fragment and subjecting the resulting fragment to colony- or plaque hybridization in a conventional manner.

The labeling of the amplified DNA fragment can be carried out using for example DIG labeling kit (#1 175 033, manufactured by Boehringer Mannheim, Co.). More specifically, a DIG-labeled amplified DNA fragment can be recovered by PCR using the amplified DNA fragment as a template and utilizing the kit.

The plaque hybridization method includes for example the following method.

The cDNA library (phage) prepared in 1) above is spread on an agar culture medium and cultivated to a final concentration of 10,000 to 20,000 plaques per one petri dish.

Hybond N$^+$ membrane (manufactured by Amersham, Co.) is placed on the petri dish with plaques formed thereon to transfer the plaque DNA onto the membrane.

The transfer membrane is subject to alkali treatment (comprising for example immersing the membrane in 1.5 M NaCl, 0.5M NaOH solution) and SDS treatment (comprising for example immersing in 2×SSC, 0.1% SDS solution), rinsing and drying, and the resulting membrane is used for hybridization as a blotted membrane with the plaque DNA immobilized thereon.

The blotted membrane is immersed in a hybridization solution [5×SSC, 0.1% Sarkosyl, 0.02% SDS, 1% blocking reagent for hybridization (manufactured by Boehringer Mannheim, Co.)] for 5 hours, and the labeled amplified DNA fragment which has been subjected to thermal treatment is added thereto for hybridization.

After hybridization, the membrane is subject to rinsing [for example, rinsing twice in 2×SSC and 0.1% SDS at room temperature for 5 minutes, and rinsing twice in 0.1×SSC and 0.1% SDS at 60° C. for 15 minutes] and blocking [for example, blocking in 1×blocking solution (manufactured Boehringer Mannheim Co.), 0.1 M maleic acid, 0.15 M NaCl, pH 7.5], and thereafter, the labeled amplified DNA is detected by a variable method, depending on the labeling mode of the labeled amplified DNA fragment, whereby an objective clone can be selected.

When a DNA fragment labeled with DIG is used, for example, reaction with anti-DIG antibody labeled with AP and subsequent alkali treatment [for example, immersing in 0.1 M Tris-HCl (pH 9.5), 0.1 M NaCl and 50 mM $MgCl_2$ solution] are carried out, and a plaque hybridized with the probe is screened on an X-ray film using a DIG luminescence detection kit (#1 363514, manufactured by Boehringer Mannheim, Co.) to select a clone containing DNA encoding 25-hydroxyvitamin $D_3$-1α-hydroxylase.

5) Recovery of DNA Encoding 25-hydroxyvitamin $D_3$-1α-hydroxylase

From the clone recovered by the screening procedure described above in 4), DNA is isolated in a conventional manner to recover DNA encoding 25-hydroxyvitamin $D_3$-1α-hydroxylase.

DNA nucleotide sequencing can be done by common nucleotide sequencing methods, for example, the dideoxy method by Sanger et. al. [Proc. Natl. Acad. Sci. USA, 74 5463 (1977)] or by sequencing by using a nucleotide sequencer such as 373A.DNA sequencer [manufactured by Perkin Elmer, Co.].

As the gene sequence of 25-hydroxyvitamin $D_3$-1α-hydroxylase thus determined includes DNA comprising the sequence represented by SEQ ID NO.3 or 5.

Based on the DNA sequence thus determined by the method, an objective DNA may be prepared by chemical synthesis with a DNA sequencer. Such DNA sequencer includes a DNA sequencer based on the thiophosphite method, manufactured by Shimadzu, and a DNA sequencer Model 1392 based on the phosphoramidits method, manufactured by Perkin Elmer, Co.

The rat-derived 25-hydroxyvitamin $D_3$-1α-hydroxylase gene as recovered above can be used to recover 25-hydroxyvitamin $D_3$-1α-hydroxylase gene derived from other animals, for example, humans, by the following method.

The DNA encoding 25-hydroxyvitamin $D_3$-1α-hydroxylase as recovered above is labeled with α-$^{32}$P-dCTP by using for example Megaprime DNA labeling kit (manufactured by Amersham Co.). In the same manner as for the method described above in 1), a cDNA library is prepared from objective animal tissues, for example human kidney.

The cDNA library is screened by colony- or plaque hybridization using the labeled DNA fragment described in 4) above as a probe.

From the clone recovered through the screening, the objective DNA is isolated by the method as described in 5) above, and the nucleotide sequence is determined.

The nucleotide sequence having high homology to the nucleotide sequence of the gene of rat 25-hydroxyvitamin $D_3$-1α-hydroxylase is defined as DNA encoding 25-hydroxyvitamin $D_3$-1α-hydroxylase derived from the objective animal.

The gene includes for example human kidney-derived DNA comprising the sequence represented by SEQ ID NO. 4 or 6.

6) Production of 25-hydroxyvitamin $D_3$-1α-hydroxylase Polypeptide

To express the DNA encoding 25-hydroxyvitamin $D_3$-1α-hydroxylase as recovered in 5) above in a host cell, the methods described in Molecular Cloning, 2-nd edition and Current Protocols in Molecular Biology, Supplement 1 to 34 and the like may be used.

More specifically, DNA recovered in 5) is modified into DNA fragments with appropriate lengths so that the DNA encoding 25-hydroxyvitamin $D_3$-1α-hydroxylase might be contained therein, by using restriction enzymes or DNases, which are then inserted into the downstream of a promoter in an expression vector, and then, the expression vector with the DNA inserted therein is introduced into a host cell appropriate for the expression vector.

Any host cell capable of expressing the objective gene may be used, including for example bacteria, yeast, animal cells and insect cells.

As the expression vector, a vector, which is autonomously replicable in the host cell or possibly inserted into the chromosome and contains a promoter at the site on which the gene of 25-hydroxyvitamin $D_3$-1α-hydroxylase can be transcribed, may be used.

When procaryotic cells such as bacteria are used as such host cells, it is preferable that an expression vector of 25-hydroxyvitamin $D_3$-1α-hydroxylase gene is autonomously replicable in the procaryotic cells and the vector is composed of a promoter, a ribosome binding sequence, DNA encoding 25-hydroxyvitamin $D_3$-1α-hydroxylase and a transcription termination sequence. A gene regulating the promoter may be contained in the vector.

Such expression vector includes for example pBTrp2, pBTac1, pBTac2 (all commercially available from Boehringer Mannheim, Co.), pKK2-2 (manufactured by Pharmacia, Co.) pSE280 (manufactured by Invitrogen, Co.), pGEMEX-1 (manufactured by Promega, Co.), pQE-8 (manufactured by QIAGEN, Co.), pKYP10 (Japanese Published Unexamined Patent Application No.110600/1983), pKYP200 [Agric. Biol. Chem., 48, 669 (1984)), pLSA1 [Agric, Biol. Chem., 53, 277 (1989)], pGEL1 [Proc. Natl. Acad. Sci., USA, 82, 4306 (1985)], pBluescript (STRATAGENE, Co.), pTrs30 (FERMBP-5407), pTrs32 (FERMBP-5408), pGHA2 (FERM BP-400), pGKA2 (FERM BP-6798), pTerm2 (Japanese Published Unexamined Patent Application No.22979/1991, U.S. Pat. No. 4,686,191, U.S. Pat. No. 4,939,094, U.S. Pat. No. 5,160, 735), pKK233-2 (manufactured by Pharmacia, Co.), pGEX (manufactured by Pharmacia, Co.), pET system (manufactured by Novagen, Co.) pSupex, pUB110, pTP5, andpC194 and the like.

Any promoter which can be expressed in host cells such as *Escherichia coli* may be used, including for example promoters derived from *Escherichia coli* and phages, for example trp promoter (Ptrp), lac promoter (Plac), $P_L$ promoter, $P_R$ promoter, PletI promoter, and $P_{SE}$ promoter; SPO1 promoter, SPO2 promoter, penP promoter and the like. Additionally, artificially designed and modified promoters, such as a promoter of two Ptrp's in series (Ptrp×2) and tac promoter may be used.

Any ribosome binding sequence may be used, as long as the sequence may be expressed in host cells such as *Escherichia coli*. Preferably, a plasmid wherein the distance between the Shine-Dalgarno sequence and the initiation codon is adjusted to an appropriate distance (for example, 6 to 18 nucleotides) may be used.

To express 25-hydroxyvitamin $D_3$-1α-hydroxylase gene of the present invention, a transcription termination sequence is not necessarily required, but preferably, a transcription termination sequence is arranged immediately below the structural gene.

Examples of the host cell include microorganisms belonging to the genus Escherichia, Serratia, Bacillus, Brevibacterium, Corynebacterium, Microbacterium, Pseudomonas, and the like. Specific examples include Escherichia coli XL1-Blue, *Eschericbia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No.49, *Escherichia coli* W3110, *Escherichia coli* NY49, *Seratia ficaria, Seratia fonticola, Seratia liquefaciens, Seratia marcescens, Bacillus subtilis, Bacillus amyloliguefaciens, Brevibacterium ammoniagenes, Brevibacterium immariophilum* ATCC 14068, *Brevibacterium saccharolyticum* ATCC 14066, *Corynebacterium glutamicum* ATCC 13032, *Corynebacterium glutamicum* ATCC 14067, *Corynebacterium glutamicum* ATCC 13869, *Corynebacterium acetoacidophilum* ATCC 13870, *Microbacterium ammoniaphilum* ATCC 15354, Pseudomonassp. D-0110 and the like.

As the method for introducing the recombinant vectors, any method for introducing DNA into the host cells may be used, including for example a method comprising the use of calcium ion [Proc. Natl. Acad. Sci. USA, 69, 2110 (1972)], protoplast method (Japanese Published Unexamined Patent Application No.2483942/1988), and methods described in Gene, 17, 107 (1982) and Molecular & General Genetics, 168, 111 (1979).

In case of using yeast bacterial strains as host cells, expression vectors for example YEp13 (ATCC 37115), YEp24 (ATCC 37051), YCp50 (ATCC 37419), pHS19, and pHS15 may be used.

As the promoter, any promoter which can be expressed in yeast bacterial strains may be used. For example, promoters such as PHO5 promoter, PGK promoter, GAP promoter, ADH promoter, gal 1 promoter, gal 10 promoter, heat shock protein promoter, MFα1 promoter, CUP 1 promoter and the like may be listed.

Host cells used include for example *Saccharomyces cerevisae, Shizosaccharomyces pombe, Kluyveromyces lactis, Trichosporon pullulans*, and *Schwanniomyces alluvius*.

As the method for introducing the recombinant vectors, any method for introducing DNA into yeast cells may be used, for example, electroporation method [Methods. Enzymol., 194, 182 (1990)], spheroplast method [Proc. Natl. Acad. Sci. USA, 84, 1929 (1978)], lithium acetate method [Journal of Bacteriology, 153, 163 (1983)], a method described in Proc. Natl. Acad. Sci. USA, 75, 1929 (1978) and the like.

In case of using animal cells as a host, the expression vector includes for example pcDNAI, pcDM8 (commercially available from Funakoshi, Co.), pAGE107 (Japanese Published Unexamined Patent Application No.22979/1991; Cytotechnology, 3, 133 (1990)), pAS3-3 (Japanese Published Unexamined Patent Application No.227075/1990), pCDM8 [Nature, 329, 840 (1987)], pcDNAI/Amp (manufactured by Invitrogen, Co.), pREP4 (manufactured by Invitrogen, Co.), pAGE103 [J. Biochem., 101, 1307 (1987)], and pAGE210.

As a promoter, any promoter which can be expressed in animal ells may be used, including for example a promoter of IE (immediate early) gene of cytomegalovirus (human CMV), an early romoter of SV40 or a promoter of metallothionein, a promoter etrovirus, a heat shock promoter and an SRα promoter. dditionally, the enhancer of the IE gene of human CMV may be sed in combination with such promoter.

Examples of the host cell include Namalwa cell, monkey cos ell, Chinese hamster CHO cell, HST5637 (Japanese Published Unexamined Patent Application No.299/1988) and the like.

As the method for introducing recombinant vector into animal cells, any method for introducing DNA into animal cells may be used, e.g., electroporation method [Cytotechnology, 3, 133 (1990)], calcium phosphate method (Japanese Published Unexamined Patent Application No.227075/1990], lipofection method [Proc. Natl. Acad. Sci., USA, 84, 7413 (1987)] and the method described in Virology, 52, 456 (1973)). Thepreparation of a transformant and cultivation of the transformant may be carried out according to the method described in Japanese Published Unexamined Patent Application No.227075/1990 or Japanese Published Unexamined Patent Application No.257891/1990.

In case of using insect cells as a host, the protein may be expressed according to the methods described in Baculovirus Expression Vectors, A Laboratory Manual, W. H. Freeman and Company, New York, 1992; Current Protocols in Molecular Biology, Supplement 1–38(1987–1997); Bio/Technology, 6, 47 (1988) and the like.

More specifically, the protein can be expressed by co-introduction of the transfer vector containing interest gene and helper DNA fragment of baculovirus into an insect cell to recover a recombinant virus in the supernatant of the culture of the insect cell and infecting an insect cell with the recombinant virus.

The transfer vector for gene introduction to be used in the method includes for example pVL1392, pVL1393, pBlue-BacIII (all manufactured by Invitrogen, Co.) and the like.

As the helper DNA fragment of baculovirus, for example, *Autographa californica* nuclear polyhedrosis virus, which is a virus infecting insects of the family Barathra, may be used.

As such insect cell, *Spodoptera frugiperda* oocytes Sf9 and Sf21 [Baculovirus Expression Vectors, A Laboratory Manual, W. H. Freeman and Company, New York, 1992], *Trichoplusiani oocytes* High 5 (manufactured by Invitrogen Co.) and the like, may be used.

The method for co-introducing the the above-described transfer vector contaning interest gene and the helper DNA fragment of baculovirus into insect cells to prepare the recombinant virus includes for example calcium phosphate method (Japanese Published Unexamined Patent Application No.227075/1990), lipofectionmethod [Proc. Natl. Acad. Sci. USA, 84, 7413 (1987)], and the like.

As the expression method of the gene, secretory production and expression of fused protein may be carried out according to the method described in Molecular Cloning, 2-nd edition and the like, in addition to direct expression.

When the gene is expressed in yeast, animal cells or insect cells, a glycosylated protein can be obtained.

The transformant thus obtained is cultivated in a culture medium to form polypeptide of the present invention in the culture, and the formed polypeptide is recovered from the culture, whereby the polypeptide of the present invention can be produced. The transformant of the present invention is cultivated in a culture medium according to a conventional method for use in cultivating hosts.

As the culture medium to cultivate a transformant recovered by using procaryotic organisms such as *Escherichia coli* or eucaryotic organisms such as yeast, any natural culture medium or any synthetic culture medium may be used, so long as it contains carbon sources, nitrogen sources, inorganic salts and the like which can be assimilated by the organisms.

Any carbon source which can be assimilated by the organisms may be used, including carbohydrates such as glucose, fructose, sucrose, molasses containing them, starch and starch hydrolysates; organic acids such as acetic acid and propionic acid; alcohols such as ethanol and propanol.

As such nitrogen sources, ammonia; ammonium salts of inorganic acids or organic salts, such as ammonium chloride, ammonium sulfate, ammonium acetate, and ammonium phosphate; other nitrogen containing compounds; peptone; meat extract; yeast extract; corn steep liquor; casein hydrolysates; soy bean meal; soy bean meal hydrolysates; various fermentation products, and digested products thereof, may be used.

As the inorganic substances, potassium dihydrogen phosphate, dipotassium hydrogen phosphate, magnesium phosphate, magnesium sulfate, sodium chloride, ferrous sulfate, manganese sulfate, copper sulfate, calcium carbonate and the like, may be used.

Cultivation is generally carried out under aerobic conditions, for example, by shaking culture or spinner culture under aeration. The cultivation is carried out at 15 to 40° C. for 16 hours to seven days at pH 3.0 to 9.0. The pH is adjusted with an inorganic or organic acid, an alkali solution, urea, calcium carbonate, ammonia and the like.

During cultivation, antibiotics such as ampicillin and tetracycline may be added to the culture medium, if necessary.

For cultivating microorganisms transformed with an expression vector prepared using an inducible promoter, an inducer may be added to the culture medium, if necessary. For cultivating microorganisms transformed with an expression vector prepared using lac promoter, for example, isopropyl-β-D-thiogalactopyranoside may be added to the medium; for cultivating microorganisms transformed with an expression vector prepared using trp promoter, forexample, indole acrylic acid may be added to the medium.

As the culture medium for cultivating a transformant recovered by using animal cells as the hosts, RPMI 1640 culture medium [The Journal of the American Medical Association, 199, 519 (1967)], Eagle's MEM culture medium [Science, 122, 501 (1952)], Dulbecco's modified MEM culture medium [Virology, 8, 396 (1959)], DMEM culture medium (manufactured by GIBCO BRL, Co.), 199 culture medium [Proceedings of the Society for the Biological Medicine, 73, 1 (1950)] for conventional use or culture media prepared by adding fetal calf serum and the like to these culture media, may be used.

Generally, cultivation is carried out in the presence of 5% $CO_2$ at pH 6 to 8 at 30 to 40° C. for 1 to 7 days.

During cultivation, if necessary, antibiotics such as kanamycin and penicillin may be added to the culture medium.

As the culture medium to cultivate transformants recovered using insect cells as the hosts, culture medium for general use, such as TNM-FH culture medium [manufactured by Pharmingen, Co.], Sf-900 II SFM culture medium [manufactured by Life Technologies, Co.], ExCell 400, ExCell 405 [both manufactured by JRH Biosciences, Co.], Grace's InsectMedium [Grace, T. C. C., Nature, 195, 788 (1962)] and the like, may be used.

Cultivation is carried out at pH 6 to 7 at 25 to 30° C. for 1 to 5 days.

During cultivation, if necessary, antibiotics such as gentamycin may be added to the culture medium.

To isolate and purify the polypeptide expressed by the method described above from the culture of the transformant, conventional isolation and purification methods of enzymes may be used.

When the polypeptide of the present invention is expressed in cells at its dissolved state, a purified sample of the polypeptide is obtained as follows. The cells are recovered through centrifugation after the cultivation, suspended in an aqueous buffer, and disrupted by means of ultrasonic oscillator, French Press, Manton Gaulin homogenizer, Dynomill and the like, to recover a cell-free extract. From the supernatant recovered by the centrifugation of the cell-free extract, a purified sample can be recovered by conventional isolation and purification methods of enzymes, singly or in combination, such as solvent extraction method, salting out methods with ammonium sulfate, etc., desalting method, precipitation methods with organic solvents, anion exchange chromatography by means of resins such as diethylaminoethyl (DEAE)-Sepharose, DIAION HPA-75 (manufactured by Mitsubishi Chemical Corporation); cation exchange chromatography by means of resins such as S-Sepharose FF (manufactured by Pharmacia, Co.); hydrophobic chromatography using resins such as butyl Sepharose and phenyl Sepharose; gel filtration methods using molecular sieves; affinity chromatography method; chromato-focusing method; electrophoresis methods such as isoelectric focusing; and the like.

When the polypeptide is expressed in cells in the form of an inclusion body, a purified sample of the polypeptide is obtained as follows. The cells are similarly recovered, disrupted, and centrifuged to recover a precipitation fraction, from which the polypeptide is recovered according to a conventional method, and the inclusion body of the polypeptide is solubilized with a polypeptide denaturant. The solubilized solution is diluted or dialyzed in a dilute solution at such an extent that the resulting solution does not contain any polypeptide denaturant or the polypeptide is not any more denatured at the concentration of the polypeptide denaturant, to renature the polypeptide into a normal steric configuration, from which a purified sample can be recovered according to the same isolation and purification method as described above.

In case that the polypeptide of the present invention or derivatives thereof such as a sugar modified product thereof are secreted extracellularly, the polypeptide or the derivatives thereof can be recovered from the culture supernatant. More specifically, the culture is treated by the method as described above, such as centrifugation, to recover a soluble fraction, and from the fraction, a purified sample is recovered using the isolation and purification method as described above.

Additionally, the polypeptide expressed by the above method may be prepared by chemical synthetic methods such as Fmoc method (fluorenylmethyloxycarbonyl method), tBoc method (t-butyloxycarbonyl method) and the like. Alternatively, the polypeptide can be prepared by utilizing peptide synthesizers commercially available from Sowa Trade (manufactured by Advanced chemTech, Co., USA), Perkin-Elmer Japan (manufactured by Perkin-Elmer, Co., USA), Pharmacia Biotech (manufactured by Pharmacia Biotech, Co., Sweden), Aroka (manufactured by protein Technology Instrument, Co., USA), KURABO (manufactured by Synthecell-Vega, Co., USA), Japan PerSeptive Limited (manufactured by PerSeptive, Co., USA), Shimadzu, Co. and the like.

7) Production of 1α, 25-dihydroxyvitamin $D_3$

The polypeptide having 25-hydroxyvitamin $D_3$-1α-hydroxylase and 25-hydroxyvitamin $D_3$ are put in an aqueous medium to form 1α,25-dihydroxyvitamin $D_3$ in the aqueous medium, and the formed 1α,25-dihydroxyvitamin $D_3$ is recovered from the aqueous medium. Thus, 1α,25-dihydroxyvitamin $D_3$ can be produced.

As a polypeptide having 25-hydroxyvitamin $D_3$-1α-hydroxylase activity, the polypeptide purified by the method described above in 6) and the microbial culture obtained by the method described above in 6) or a treated product of the culture obtained by treating the culture in various ways and the like, may be used.

Examples of the treated product of the culture broth include a concentrated product of the culture, a dried product of the culture, a culture supernatant obtained by centrifuging the culture, a concentrated product of the culture supernatant, an enzyme preparation obtained from the culture supernatant, cells (including microbial cells) obtained by centrifuging the culture, a dried product of the cells, a freeze-dried product of the cells, a surfactant- treated product of the cells, an ultrasonic-treated product of the cells, a mechanically disrupted product of the cells, a solvent-treated product of the cells, an enzyme-treated product of the cells, a protein fraction of the cells (fractions having 25-hydroxyvitamin $D_3$-1α-hydroxylase activity), an immobilized product of the cells and an enzyme preparation obtained by extraction from the cells.

The concentration of the polypeptide having 25-droxyvitamin $D_3$-1α-hydroxylase activity is 0.01 to 50 g/l, referably 0.05 to 10 g/l, as wet cells.

The aqueous medium includes water, buffers such as phosphate salts, carbonate salts, acetate salts, borate salts, citrate salts, and Tris; and aqueous solutions containing organic solvents such as alcohols such as methanol and ethanol; esters such as ethyl acetate; ketones such as acetone; amides such as acetoamide. If necessary, surfactants such as Triton X-100 (manufactured by Nakarai Tesque, Co.) and Nonion HS204 (manufactured by Nippon Oils and Fats Co.), or organic solvents such as toluene and xylene may be added at about 0.1 to 20 g/l.

The concentration of 25-hydroxyvitamin $D_3$ is 0.01 to 50 g/l, preferably 0.01 to 10 g/l.

1α, 25-dihydroxyvitamin $D_3$ can be produced by adding polypeptide having 25-hydroxyvitamin $D_3$-1α-hydroxylase activity and 25-hydroxyvitamin $D_3$. The reaction is carried out at 15 to 80° C., preferably 20 to 40° C., at pH 3 to 11, preferably pH 4 to 9, for 5 minutes to 96 hours.

8) Preparation of an Antibody Recognizing 25-hydroxyvitamin $D_3$-1α-hydroxylase A purified product of the whole length or a partial fragment of the protein obtained by the method described in the above in 6) or a peptide having a partial amino acid sequence of the protein of the present invention is used as the antigen. The antigen is administered to animal by subcutaneous, intravenous or intraperitoneal injection together with an appropriate adjuvant (for example, complete Freund's adjuvant, aluminum hydroxide gel, pertussis vaccine, or the like).

Examples of the animals used include rabbits, goats, 3- to 20-weak-old rats, mice, hamsters and the like.

Preferable dosage of antigen is 50 to 100 µg per animal.

When a peptide is used as the antigen, it is preferred to use the peptide as the antigen after binding it covalently to a carrier protein, such as keyhole limpet haemocyanin, bovine thyroglobulin or the like. The peptide used as the antigen can be synthesized using a peptide synthesizer.

Administration of the antigen is carried out 3 to 10 times at one- to two-week intervals after the first administration. A blood sample is recovered from the fundus of the eye 3 to 7 days after each administration, and the serum is tested, for example, by enzyme immunoassay (Enzyme-linked Immunosorbent Assay (ELISA), published by Igaku Shoin (1976); Antibodies—A Laboratory Manual, Cold Spring Harbor Laboratory (1988)) as to whether it is reactive with the antigen used for immunization. A non-human mammal whose serums shows a sufficient antibody titer against the antigen used for immunization is submitted for use as the supply source of serum or antibody producing cells.

A polyclonal antibody can be prepared by isolating and purifying it from the serum.

A monoclonal antibody can be prepared by preparing a hybridoma through fusion of the antibody producing cells with myeloma cells of a non-human mammal and culturing the hybridoma, or administering the hybridoma to an animal to induce ascites tumor in the animal, and then isolating and purifying it from the culture medium or ascitic fluid.

Examples of the antibody producing cells include spleen cells, lymph nodes and antibody producing cells in peripheral blood. Particularly, spleen cells are preferred.

Examples of the myeloma cells include cell lines derived from mouse, such as P3-X63Ag8-U1 (P3-U1) cell line [Current Topics in Microbiology and Immunology, 18, 1–7 (1978)], P3-NS1/1-Ag41 (NS-1) cell line [European J. Immunology, 6, 511–519 (1976)], SP2/O-Ag14 (SP-2) cell line [Nature, 276, 269–270 (1978)], P3-X63-Ag8653 (653) cell line [J. Immunology, 123, 1548–1550 (1979)], P3-X63-Ag8 (X63) cell line [Nature, 256, 495–497 (1975)] and the like, which are 8-azaguanine-resistant mouse (BALB/c) myeloma cell lines.

Hybridoma cells can be prepared in the following manner.

Antibody producing cells and myeloma cells are fused, suspended in HAT medium (normal medium supplemented with hypoxanthine, thymidine and aminopterin) and then cultured for 7 to 14 days. After the culturing, a portion of the culture supernatant is sampled and tested, for example, by enzyme immunoassay to select those which can react with the antigen but not with protein which does not contain the antigen. Thereafter, cloning is carried out by limiting dilution analysis, and a hybridoma which shows stable and high antibody titer by enzyme immunoassay is selected as monoclonal antibody producing hybridoma cells.

With regard to the method for the isolation and purification of the polyclonal antibody or monoclonal antibody, centrifugation, ammonium sulfate precipitation, caprylic acid precipitation, or chromatography using a DEAE-Sepharose column, an anion exchange column, a protein A or G column, a gel filtration column and the like may be employed alone or as a combination thereof.

9) Utilization of the Polypeptide and the DNA Encoding the Polypeptide of the Present Invention and the Antibody Recognizing the Polypeptide of the Present Invention (1) The polypeptide of the present invention can be utilized for producing 1α, 25-dihydroxyvitamin $D_3$ as active type vitamin $D_3$.

(2) The whole length or partial fragments of the polypeptide of the present invention can be utilized as an antigen against the antibody recognizing 25-hydroxyvitamin $D_3$-1α-hydroxylase.

(3) By administering the whole length of the 25-hydroxyvitamin $D_3$-1α-hydroxylase or partial fragments thereof having the activity into biological organisms, diseases due to the decrease of the enzyme protein, such as osteoporosis, can be treated therapeutically.

(4) By using the DNA of the present invention, the mRNA of 25-hydroxyvitamin $D_3$-1α-hydroxylase gene can be detected by Northern hybridization method (Molecular Cloning, 2-nd edition), PCR method [PCR Protocols, Academic Press (1990)], and RT-PCR method and the like.

The diagnostic method for assaying the expression level of the mRNA of the gene of 25-hydroxyvitamin $D_3$-1α-hydroxylase by utilizing the detection method, is useful for suppressing the onset of adult diseases such as osteoporosis induced by the decrease of active type vitamin $D_3$ and is also effective for early diagnosis of genetic diseases due to congenital deficiency of the 25-hydroxyvitamin $D_3$-1α-hydroxylase gene.

According to Northern hybridization method, the expression level of mRNA is assayed on the basis of the label of a probe hybridized, for example, on the basis of the radioactivity in case of labeling with for example $^{32}P$ or the fluorescence in case of fluorescent labeling. The expression level of mRNA is assayed, on the basis of the fluorescence of a DNA specific fluorescent dye, for example ethidium bromide and Cyber Green 1 which is used for staining amplified fragments.

(5) The DNA of the present invention is inserted into virus vectors such as retrovirus and adenovirus and other vectors, and the resulting DNA can be used for therapeutic treatment according to gene therapy.

(6) By using the anti-25-hydroxyvitamin $D_3$-1α-hydroxylase antibody of the present invention, 25-hydroxyvitamin $D_3$-1α-hydroxylase can be detected and assayed in samples of blood, some organs, cells and the like. Specifically preferable methods therefor include ELISA method by using microtiter plates, fluorescent antibody methods, Western blot method and the like; additionally, immuno-histological staining by using pathological sections may also be utilized. Thus, the antibody of the present invention is useful for the diagnosis of diseases such as osteoporosis, due to the decrease of the expression of vitamin $D_3$-1α-hydroxylase, the diagnosis of the onset thereof and early prediction of the possibility of the onset thereof and the like. Similarly, the antibody is also useful as a laboratory reagent for research works for the protein.

(7) By using the antibody of the present invention, polypeptides having 25-hydroxyvitamin $D_3$-1α-hydroxylase activity are immuno-histologically stained, and thus, an immuno-histological staining agent containing the antibody can be provided.

(8) By using the DNA of the present invention and through the hybridization thereof with the genome DNA, the DNA in the promoter region of the gene can be cloned. By using DNA fragments in the promoter region, molecules involved in the regulation of the expression of the gene can be screened and analyzed.

The present invention will now be described in detail in the following examples. When kits were used in individual procedures, experiments were progressed according to the protocols attached to the kits, unless otherwise stated specifically. Fundamental genetic manipulation techniques were according to Molecular Cloning, 2-nd edition.

EXAMPLES

Example 1

Preparation of Kidney From Rats Fed with Vitamin $D_3$ Deficient Diet

Immediately after weaning, four male SD rats were given vitamin $D_3$ deficient diet for 3 weeks (age 6 weeks).

DIET 11 [Suda, et. al., J. Nutrition, 100, 1049 (1970); commercially available as Purified diet for Rat from Teklad Co, Madison, Wis., USA] wasusedas thevitamin $D_3$ deficientdiet. The diet was vitamin D deficient and low calcium diet at a calcium content of 0.03% and a phosphate content of 0.6%.

Deionized water was used for supplementing the rats with water.

48 hours prior to sacrifice, 1α, 25-dihydroxyvitamin $D_3$ (manufactured by Calviochem, Co., CA, USA) was intravenously injected at 1 μg/rat into the rats.

After the designed dieting term was terminated, the rats were anesthetized with ether. From the abdominal aortas of the rats, blood was drawn out, and then, the rats were sacrificed to death by phlebotomy and immediately thereafter, the rats were autopsied to resect the kidneys.

The kidneys were rinsed in PBS [containing NaCl (8 g), KCl (0.2 g), $NaH_2PO_4.12H_2O$ (2.9 g) and $KH_2PO_4$ (0.2 g) per one liter), and the resulting kidneys were frozen in liquid nitrogen.

As a control group, rats were given normal diet (Rat diet containing calcium (0.5 g), phosphate (0.6 g) and vitamin $D_3$ (200 IU) per 100 g) in a similar fashion, and then, the kidneys were prepared by the same method as described above. The resulting kidneys were used as kidneys from rats with no activity induction.

Example 2

Preparation of mRNA From Rat Kidneys

The kidneys prepared from the rats fed with the vitamin $D_3$ deficient diet and the kidneys derived from the rats fed with normal diet, weighed 0.78 g and 0.94 g, respectively, were rinsed in PBS and were then frozen in liquid nitrogen. The frozen kidneys can be stored at −80° C.

The frozen kidneys were cut into pieces in liquid nitrogen with a wearing blender, until the tissues were hashed into sand size form. Then, the liquid nitrogen was evaporated.

The sand-like tissues were homogenized in ice cooling with a homogenizer (Digital Homogenizer; manufactured by Inouchi, Co.), while adding thereto 35 ml of 5.5 M GTC solution (containing 324.5 g of guanidine isothiocyanate, 3.7 g of sodium citrate, and 3.3 g of Sarkosyl in 500 ml) and 492 μl of 2-mercaptoethanol, and the homogenate in suspension was passed four times through an injection needle of gauge 18 arranged on a 50-ml injection cylinder. The suspension was then transferred into a 15-ml centrifuge tube, for centrifugation at 6,000 rpm at 20° C. for 10 minutes, to recover the supernatant. The supernatant was then overlaid in 16-ml portions on a CsTFA preparative solution [a mixture solution of CsTFA solution (100 ml) manufactured by Pharmacia, Co., 82.06 ml of 0.25 M EDTA solution (pH 7.0), and 23.09 ml of $H_2O$] in a 40-ml polyallomer tube for ultracentrifugation, and the tube was then ultra-centrifuged under conditions of 25,000 rpm and 18° C. for hours.

After discarding the supernatant, the tube was cut at the position of about 1.5 cm from the bottom of the tube, and the resulting precipitate was dissolved in 0.6 ml of 4M GTC solution [a mixture solution of 5.5M GTC solution (4 ml), 1.5 ml of $H_2O$, and 56 μl of 2-mercaptoethanol].

The dissolved solution was centrifuged at 14,000 rpm for 15 seconds, to recover the supernatant.

After adding 15 μl of 1M sodium acetate and 0.45 ml of ethanol to the supernatant and thereby suspending the precipitate, the resulting suspension was centrifuged to recover the precipitate.

The precipitate was rinsed in 70% ethanol, suspended in 1 ml of TE buffer [10 mM Tris-HCl (pH 8.0), 1 mM EDTA-NaOH (pH 8.0)], and centrifuged at 14,000 rpm for 15 seconds, to recover the supernatant.

Adding a 2.5-fold volume of 70% ethanol to the supernatant, followed by centrifugation, the resulting precipitate was recovered.

The precipitate was rinsed in 70% ethanol and was then dissolved in 500 μl of TE buffer.

Through the procedure, the whole RNA was recovered from the kidneys from the rats with activity induction and the rats with no activity induction, which was calculated as 639 μg and 918 μg, respectively, on the basis of the absorbance at 260 nm.

The whole RNA solution (150 μl) derived from the rats with activity induction was effected with thermal treatment at 65° C. for 5 minutes, which was immediately cooled in ice. To the solution were added 0.5 ml of 5M NaCl and 0.15 g oligo dTcellulose (manufacturedbyCollaborativeResearch, Co., Type 3) equilibrated with TE/NaCl [10 mM Tris-HCl (pH 7.5), 500 mm NaCl], to adsorb the whole RNA onto the cellulose.

The cellulose was packed in a column, through which the TE/NaCl solution was passed for washing the column, followed by elution of mRNA with TE solution of 0.5 ml, to fractionate and collect the eluate in 200 μl-fractions.

From the individual fractionated solutions, 2 μl portions were sampled, followed by addition of 1 μg/ml ethidium bromide (20 μl), to detect luminescent sampled solutions under ultraviolet irradiation.

Ethanol was added to the fractionated solutions corresponding to the luminescent sampled solutions, to recover precipitates.

The precipitates were rinsed in 80% ethanol and suspended in TE buffer.

Through the procedures, mRNA of 14.3 μg was recovered from the kidneys of the rats with activity induction.

Example 3

Preparation of cDNA Library

By using ZAP-cDNA synthesis kit (#200400) manufactured by Stratagene Co., a cDNA library was constructed according to the instruction manual attached to the kit.

By using 4 μg of mRNA derived from the rats with activity induction as prepared in Example 2, fist strand DNA was synthesized through reverse-transcriptase reaction, and after RNase reaction, second strand DNA was synthesized with DNA polymerase I.

Under high temperature conditions, PfuDNA polymerase reaction was effected to make the termini of the cDNA to blunt end.

By ligating an EcoRI adapter fragment to the cDNA for phosphorylation and digesting the resulting cDNA with XhoI, a cDNA fragment with EcoRI-XhoI cleavage sites on both the termini was prepared.

The cDNA fragment was inserted into the EcoRI-XhoI site of λ ZAP II, and by subsequent packaging with Giga pack Gold Packaging Kit (manufactured by Stratagene, Co.) and infection by using *Escherichia coli* host XL1-Blue, MRF' strain and helper phage VCS257, a cDNA library was constructed.

Example 4

Selection of a Clone Harbouring mRNA Molecule Specifically Expressed in the Kidneys of the Rats with Induced Activity The amino acid sequences of the rat-derived hydroxylase of the position 25 of vitamin $D_3$ and the hydroxylase of the position 24 thereof were previously reported, and among the regions well preserved in these vitamin $D_3$ hydroxylases of the family P450, the partial amino acid sequences of the adrenodoxin binding region (region A) essential for the enzyme activity and of the hem binding region (region H) were selected, and on the basis of the DNA sequences were designed a sense primer and an antisense primer for PCR amplification of the gene in the regions.

More specifically, DNA comprising the nucleotide sequence represented by SEQ ID No.7 corresponding to the region A was used as the sense primer; and DNA comprising the nucleotide sequence represented by SEQ ID NO.8 corresponding to the region H was used as the antisense primer.

By using the ZAP-cDNA synthesis kit (#200400) manufactured by Stratagene Co. and 4 μg of the mRNA derived from the rats having activity induction, first strand DNA was synthesized with a primer random hexamer.

By using the first strand DNA as the template, the DNA comprising the nucleotide sequence represented by SEQ ID NO.7 as the sense primer and the DNA comprising the nucleotide sequence represented by SEQ ID NO.8 as the antisense primer and by utilizing RT-PCR kit manufactured by Stratagene, Co., PCR was effected.

By using DNA Thermal Cycler 480 manufactured by Perkin Elmer, Co., PCR was effected at 35 cycles, each cycle composed of 94° C. for 30 seconds, 42° C. for one minute and 72° C. for one minute.

The reaction product was analyzed by agarose gel electrophoresis, and a 255-bp amplification fragment (AH fragment) was observed. By using a DNA purification kit (manufactured by Bio Rad, Co.), the fragment was extracted from agarose, which was then inserted into pCRII vector (manufactured by Invitrogen, Co.).

From the whole RNAs derived from the rats induced with 25-hydroxyvitamin $D_3$-1α-hydroxylase activity and the non-induced rats were prepared poly(A)$^+$RNAs, which were then subject individually to agarose electrophoresis, to transfer the electrophoresed mRNAs onto membrane filters in a conventional manner.

By using these membrane filters, Northern hybridization was effected by using the amplified AH fragment as the probe.

The amplified AH fragment was hybridized only when the membrane filter prepared from the mRNA derived from the rats with activity induction was used.

The AH fragment had nucleotide sequences corresponding to the regions A and H.

By using the AH fragment and 3' RACE system kit manufactured by BRL, Co., a PCR amplified fragment containing the 3' noncoding region of the DNA encoding the 25-hydroxyvitamin $D_3$-1α-hydroxylase was recovered by the following method.

By using the Oligo dT/AUAP primer attached to the 3' RACE system kit manufactured by BRL, Co. and 4 μg of the mRNA from the rats with activity induction as recovered in Example 2, cDNA was synthesized.

The cDNA was used as a template.

Based on the sequence of the AH fragment amplified above, DNA comprising the nucleotide sequence represented by SEQ ID NO.9 was synthesized and used as a sense primer.

The AUAP primer attached to the 3' RACE system kit manufactured by BRL, Co. was used as an antisense primer.

By using the template, the sense primer and the antisense primer, PCR was effected at 35 cycles, each cycle composed of 94° C. for one minute, 55° C. for one minute and 72° C. for 2 minutes.

The reaction product was analyzed by agarose gel electrophoresis, and an amplified fragment of 1.3 kb (A3 fragment) was observed. By using a DNA purification kit (manufactured by Bio Rad, Co.), the fragment was extracted from agarose, which was then inserted into pCRII vector.

In the same manner as for the AH fragment, the A3 fragment was specifically hybridized with the mRNA from the rats with activity induction.

The A3 fragment contained almost whole length of the AH fragment.

Example 5

Recovery of DNA Encoding 25-hydroxyvitamin $D_3$-1α-hydroxylase

The cDNA phage library prepared in Example 3 was spread on an agar medium and cultivated to a final concentration of 10,000 to 20,000 plaques per one petri dish.

HybondN$^+$ membrane (manufactured by Amersham, Co.) was placed on each of the petri dishes with the plaques formed thereon, to transfer the plaque DNA onto the membrane. Two transcription membranes were prepared per one petri dish.

The transcription membranes were subject to alkali treatment (immersion in 1.5 M NaCl and 0.5 M NaOH) and SDS treatment (immersion in 2×SSC and 0.1% SDS solution), rinsed and dried, and then, the resulting membranes with plaque DNA immobilized thereon were used as blotting membranes for the following hybridization.

By using DIG labeling kit (#1 175 033; manufactured by Boehringer Mannheim, Co.) and 2 ng each of the AH fragment and A3 fragment as templates, PCR was effected, to recover DIG labeled AH fragment or A3 fragment.

PCR was effected under conditions of 30 cycles, each cycle of a process of 94° C. for one minute, 50° C. for one minute and 72° C. for one minute.

The resulting DIG labeled AH fragment and DIG labeled A3 fragment were used as the following probes.

The blotting membranes prepared above were immersed in a hybridization solution [5×SSC, 0.1% Sarkosyl, 0.02% SDS, 1% hybridization blocking solution (manufactured by Boehringer Mannheim, Co.)] at 60° C. for 5 hours, followed by addition of thermally treated DIG labeled probe (10 μl/10 ml-hybridization solution), for overnight hybridization at 65° C.

After hybridization, the membranes were subject to rinsing (rinsing twice in 2×SSC and 0.1% SDS at room temperature for minutes, rinsing twice in 0.1×SSC and 0.1% SDS at 60° C. for 15 minutes), blocking [effected by using 1×blocking solution (manufactured by Boehringer Mannheim, Co.), 0.1M maleic acid, 0.15M NaCl, pH 7.5], reaction with AP labeled anti-DIG antibody (effected according to the protocol by Boehringer Mannheim, Co.), and alkali treatment [0.1M Tris-HCl (pH 9.5), 0.1M NaCl and 50 mM $MgCl_2$], and by using thereafter DIG luminescence detection kit (#1 363 514; manufactured by Boehringer Mannheim, Co.), plaques hybridizable with the probes were screened on an X-ray film.

By using firstly the DIG labeled AH fragment as the DIG labeled probe to select plaques hybridizable with the fragment and by subsequently using the DIG labeled A3 fragment, plaques hybridizable with the fragment were selected from the plaques described above.

The plaques selected at each stage were again inoculated on petri dishes, and then, it was confirmed that these were hybridizable. By PCR using both the primers of the region A and AUAP, additionally, it was confirmed that the plaques had the nucleotide sequence of the A3 fragment.

After screening of 35 petri dishes in total, finally, four plaques (Nos.221, 522, 411, 111) were selected.

From individual plaque clones was extracted DNA, which was then ligated to pBluescript vector by using rapid excision kit (#211204; manufactured by Stratagene, Co.), and subsequently, the nucleotide sequence of DNA inserted into the clone was analyzed by using M13 primer.

By the analysis with the clone No.221, DNA comprising a nucleotide sequence of 2469 bp was observed, as represented by SEQ ID No.5.

An open reading frame (referred to as ORF hereinafter) encoding 501 amino acids was observed in the DNA, in which amino acid sequences believed as the hem binding region and adrenodoxin binding region in common with the P450 family protein were present.

Example 6

Expression of Isolated 25-hydroxyvitamin $D_3$-1α-hydroxylase Gene in Animal Cells From the clone No.221 described in Example 5 was prepared a plasmid, which was subsequently digested with HindIII and XbaI. Expression vector pcDNA3 (manufactured by Invitrogen, Co.) for animal cells was similarly digested with HindIII and XbaI.

The cleavage fragments recovered above were individually subject to agarose electrophoresis, which were thereby separated and extracted.

The resulting DNA fragments from the vector and the inserted gene fragment were ligated together, by using a DNA ligation kit(manufactured by TaKaRa Brewery), to recover a ligated plasmid.

By using the plasmid, *Escherichia coli* strain DH5α was transformed, and thereafter, an ampicillin resistant strain was selected, from which the plasmid was extracted according to a known method.

Based on the analysis of the plasmid by restriction cleavage, it was confirmed that the plasmid inserted the objective gene. The plasmid was named pCMD3R.

By electroporation [Potter et. al., Proc. Natl. Acad. Sci. USA, 81, 716 (1984)], pCMD3Rwas introducedintoanimal cell, to be expressed therein as follows. COS7 cell was cultivated in a DMEM culture medium (manufactured by GIBCO BRL, Co.) supplemented with 10% FCS (fetal calf serum) in a petri dish for 2 days.

After cultivation, the cells were peeled off from the petri dish by trypsin treatment, and the cells were rinsed in PBS and then suspended in 0.5 ml of KPBS (137 mM KCl, 2.7 mM NaCl, 8.1 mM $Na_2HPO_4$, 1.5 mM $NaH_2PO_4$, 4 mM $MgCl_2$), to a final concentration of 2 to $6.0 \times 10^6$/ml.

The suspension and 15 μg of pCMD3R plasmid were mixed together in a pulser cuvette (manufactured by BIO-RAD, Co.) with a groove width of 0.4 cm, and the resulting mixture was then applied to an electroporation system Gene pulser (manufactured by BIO-RAD, Co.) for pulse loading under conditions of 960 μF and 0.22 kV, to introduce the DNA into the cell.

The DNA introduced cell was suspended in 10 ml of DMEM culture medium containing 10% FCS, for cultivation in a 5% $CO_2$ incubator at 37° C. for 48 to 72 hours.

By discarding the culture in the petri dish and rinsing the cell twice in PBS, the cell was scraped off with a scraper, followed by centrifugation to collect the cell.

Example 7

Recovery of Human-derived 25-hydroxyvitamin $D_3$-1α-hydroxylase Gene

From 1.2 g of tissue resected from human kidney cancer, the whole RNA (750 μg) was recovered according to the method described in Example 2, and 9.5 μg of mRNA was recovered from the whole RNA.

By using 5 μg of the mRNA, a human cDNA library was constructed by the method described in Example 3.

According to the method described in Example 5, DNA encoding the human derived 25-hydroxyvitamin $D_3$-1α-hydroxylase was recovered.

The whole length of the rat vitamin $D_3$ hydroxylase gene of 2469 bp as isolated in Example 5 was DIG labeled according to the method described in Example 5, which was then used as a probe.

Hybridization was effected overnight in a hybridization solution containing formamide at 40% under a condition of 42° C.

Through the hybridization, four clones were selected.

According to the method described in Example 5, DNA was extracted from these clones, to analyze the nucleotide sequence of the DNA inserted into the clones.

The DNA had the nucleotide sequence represented by SEQ ID NO.6. In the DNA fragment was observed ORF encoding a peptide of 508 amino acids.

The peptide had an amino acid sequence in common with the rat-derived 25-hydroxyvitamin $D_3$-1α-hydroxylase in terms of 413 amino acid residues, and contained amino acid sequences possibly corresponding to the hem binding region and adrenodoxin binding region, commonly observed in the P450 family protein.

Additionally, the DNA sequence included a sequence of 1724 residues, which is the same as the sequence derived from rats, and therefore, it was indicated that the DNA had high homology.

Example 8

Expression of Rat-derived Vitamin $D_3$-1α-hydroxylase Gene and Assay of the Activity According to the method of Example 6, gene expression plasmid carrying the rat-derived vitamin $D_3$-1α-hydroxylase gene, namely pCMD3R, was introduced into COS-7 cell by electroporation.

The gene-introduced cells of $5 \times 10^5$ in number were cultivated in 10 ml of a DMEM culture medium containing 10% FCS for 24 hours, and then, the culture medium was exchanged to a DMEM culture medium (8 ml) containing 1% FCS, followed by addition of [26, 27-$^3$H]-25-hydroxyvitamin $D_3$ (manufactured by Amersham, Co.) at 2000 Bq/3 μl-methanol solution, and then, the resulting mixture was cultivated for 24 hours.

After cultivation, vitamin $D_3$ metabolites were extracted from the culture supernatant and the cells by the Bligh & Dyer's method [Can. J. Biochem., 37, 911 (1959)]. More specifically, the culture was transferred into a 50-ml centrifuge tube equipped with a screw cap, while 10 ml methanol was added into the petri dish, to scrape the cells with a scraper, and the cells were then transferred into the centrifuge tube. Methanol (10 ml) was again added into the petri dish, to suspend the cells remaining in the petri dish, and the resulting suspension was thoroughly transferred into the centrifuge tube.

Chloroform (10 ml) was added into the centrifuge tube for thorough mixing, followed by further addition of 10 ml of chloroform and subsequent complete re-mixing, and the resulting tube was left to stand to separate a chloroform layer from an aqueous layer.

The chloroform extract solution in the separated chloroform layer was placed in another centrifuge tube, followed by further addition of 10 ml of chloroform to the remaining aqueous layer, for mixing and extraction in the same manner, and the resulting chloroform extract solution was combined together with the previously recovered chloroform extract solution.

Distilled water was added into the chloroform extract solution to a final total volume of 60 ml, followed by addition of two drops of saturated sodium chloride solution and subsequent sufficient mixing.

The mixture solution was centrifuged, to separate the chloroform layer from the aqueous layer.

The resulting chloroform layer fraction was concentrated in nitrogen gas stream to recover the residue.

The residue was dissolved in 400 µl of a mixture solution iso-propanol/methanol/n-hexane=6:6:88.

With HPLC system 880 PU manufactured by JASCO, Co. with TSK silica gel 150 column (4.6×250 mm; manufactured by Toso, Co.) arranged thereon, the resulting solution was subject to analysis under conditions such that the mixture solution iso-propanol/methanol/n-hexane=6:6:88 was used as the mobile phase at a flow rate of 1 ml/minute. On comparison with the elution time of a standard substance, vitamin $D_3$ metabolites were identified.

Similarly, vitamin $D_3$ metabolites were identified by using a vector pcDNA3 which does not carry the gene of the present invention.

The results are shown in FIG. 1.

"A" represents the analytical results of metabolites in the cells introduced with pcMD3R; and "B" represents the analytical results of metabolites in the cells introduced with pcDNA3. Because 1α, 25-hydroxyvitamin $D_3$ was detected only in the cells introduced with pcMD3R carrying the gene of the present invention, it was indicated that only the cells had 25-hydroxyvitamin $D_3$-1α-hydroxylase activity, which further indicates that the gene of the present invention encodes 25-hydroxyvitamin $D_3$-1α-hydroxylase.

INDUSTRIAL APPLICABILITY

In accordance with the present invention, the following can be provided; a polypeptide having 25-hydroxyvitamin $D_3$-1α-hydroxylase activity, being useful for the prevention, diagnosis and therapeutic treatment of adult diseases such as osteoporosis induced by the decrease of active type vitamin $D_3$, DNA encoding the polypeptide, a recombinant DNA prepared by inserting the DNA in a vector, a transformant carrying the recombinant DNA, a method for preparing 25-hydroxyvitamin $D_3$-1α-hydroxylase by using the transformant, a method for preparing 1α, 25-dihydroxyvitamin $D_3$ by using the polypeptide having 25-hydroxyvitamin $D_3$-1α-hydroxylase activity, and an antibody recognizing the polypeptide.

What is claimed is:

1. An isolated polypeptide comprising an amino acid sequence represented by SEQ ID NO.2.

2. A DNA encoding a polypeptide comprising an amino acid sequence represented by SEQ ID NO. 2.

3. A recombinant DNA prepared by inserting the DNA according to claim 2 into a vector.

4. A transformant carrying a recombinant DNA according to claim 3.

5. The DNA according to claim 2, wherein the DNA is DNA comprising a nucleotide sequence represented by SEQ ID NO.4.

6. A recombinant DNA prepared by inserting the DNA according to claim 3 into a vector.

7. A transformant carrying a recombinant DNA according to claim 6.

8. A method for producing 25-hydroxyvitamin $D_3$-1α-hydroxylase, comprising:

cultivating the transformant according to claim 4 in a medium to produce 25-hydroxyvitamin $D_3$-1α-hydroxylase in the culture; and recovering said 25-hydroxyvitamin $D_3$-1α-hydroxylase from the resulting culture.

9. A method for producing 1α, 25-dihydroxyvitamin $D_3$, comprising:

putting the polypeptide according to claim 1 and 25-hydroxyvitamin $D_3$ in an aqueous medium to produce 1α, 25-dihydroxyvitamin $D_3$ in the aqueous medium; and recovering said 1α, 25-dihydroxyvitamin $D_3$ from the aqueous medium.

* * * * *

UNITED STATES PATENT AND TRADEMARK OFFICE
CERTIFICATE OF CORRECTION

PATENT NO. : 6,274,359 B1
DATED : August 14, 2001
INVENTOR(S) : Hideharu Anazawa et al.

It is certified that error appears in the above-identified patent and that said Letters Patent is hereby corrected as shown below:

Title page,
Insert "[*] Notice: This patent issued on a continued prosecution application filed under 37 CFR 1.53(d), and is subject to the twenty year patent term provisions of 35 U.S.C. 154(a)(2).

Column 1,
Line 61, "1α,25-dihydroxyvitamin" should read -- 1α, 25-dihydroxyvitamin --.

Column 2,
Line 65, "Chapter 8." should read -- Chapter 8, --.

Column 3,
Lines 27, 29 and 54, "2-nd" should read -- 2nd --.

Column 5,
Line 13, "poly(A)+RNAs electrophoresed" should read -- electrophoresed poly (A)+RNAs --; and
Line 65, "subject" should read -- subjected --.

Column 6,
Line 26, "373A.DNA" should read -- 373A•DNA --.

Column 7,
Line 1, 2-nd" should read -- 2nd --;
Lines 21 and 22, "is" should read -- be --;
Line 37, "(FERMBP-5407)," should read -- (FERM BP-5407), -- and
Line 38, "(FERMBP-5408)," should read -- (FERM BP-5408), --.

Column 8,
Line 3, "Eschericbia" should read -- Escherichia --;
Line 15, "Pseudomonassp." should read -- Pseudomonas sp. --;
Line 57, "ells" should read -- cells --;
Line 59, "romoter" should read -- promoter --;
Line 60, "etrovirus," should read -- retrovirus, --;
Line 61, "dditionally," should read -- Additionally, --;
Line 62, "sed" should read -- used --; and
Line 65, "ell," should read -- cell, --.

UNITED STATES PATENT AND TRADEMARK OFFICE
CERTIFICATE OF CORRECTION

PATENT NO.    : 6,274,359 B1
DATED         : August 14, 2001
INVENTOR(S)   : Hideharu Anazawa et al.

It is certified that error appears in the above-identified patent and that said Letters Patent is hereby corrected as shown below:

Column 9,
Line 7, "Thepreparation" should read -- The preparation --;
Line 36, "the" (second occurrence) should be deleted; and
Line 46, "2-nd" should read -- 2nd --.

Column 10,
Line 31, "forexample," should read -- for example, --; and
Line 54, "InsectMedium" should read -- Insect Medium --.

Column 11,
Line 27, "at" should read -- to --;
Line 61, "1α,25-dihydroxyvitamin" should read -- 1α, 25-dihydroxyvitamin --;
Line 62, "1α,25-dihydroxyvitamin" should read -- 1α, 25-dihydroxyvitamin --; and
"1α,25-" should read -- 1α, 25 --.

Column 12,
Line 11, "surfactant– treated" should read -- surfactant-treated --;
Line 20, "25-droxyvitamin" should read -- 25-hydroxyvitamin --;
Line 21, "referably" should read -- preferably --; and
Line 67, "shows" should read -- show --.

Column 13,
Line 62, "2-nd" should read -- 2nd --.

Column 14,
Line 51, "2-nd" should read -- 2nd --;
Line 62, "wasusedas thevitamin" should read -- was used as the vitamin --; and
Line 63, "cientdiet." should read -- cient diet. --.

Column 15,
Line 10, "$NaH_2PO_4.12H_2O$" should read -- $NaH_2PO_4 \bullet 12H_2O$ --;
Lines 39 and 42, "The" should read -- ¶ The --.

Column 16,
Line 11, "To" should read -- ¶ To --.

Column 17,
Line 36, "subject" should read -- subjected --.

UNITED STATES PATENT AND TRADEMARK OFFICE
CERTIFICATE OF CORRECTION

PATENT NO. : 6,274,359 B1
DATED : August 14, 2001
INVENTOR(S) : Hideharu Anazawa et al.

It is certified that error appears in the above-identified patent and that said Letters Patent is hereby corrected as shown below:

Column 18,
Line 47, "subject" should read -- subjected --; and
Line 49, "minutes," should read -- 5 minutes, --.

Column 19,
Line 30, "subject" should read -- subjected --;
Line 34, "kit(manufactured" should read -- kit (manufactured --; and
Line 44, "pCMD3Rwas introducedintoanani-" should read -- pCMD3R was introduced into an ani- --.

Column 20,
Line 61, "10 ml" should read -- 10 ml of --.

Column 21,
Line 27, "subject" should read -- subjected --.

Column 43,
Lines 36 and 43, "recombinant DNA prepared by inserting" should read -- vector comprising --;
Line 37, "claim 2 into a vector." should read -- claim 2. --; and
Line 44, "claim 3 into a vector." should read -- claim 3. --.

Signed and Sealed this

Eighteenth Day of June, 2002

Attest:

*Attesting Officer*

JAMES E. ROGAN
*Director of the United States Patent and Trademark Office*